(12) United States Patent
Finkelstein et al.

(10) Patent No.: US 6,696,601 B2
(45) Date of Patent: Feb. 24, 2004

(54) HYDRATE FORMS OF ALENDRONATE SODIUM, PROCESSES FOR MANUFACTURE THEREOF, AND PHARMACEUTICAL COMPOSITIONS THEREOF

(75) Inventors: Nina Finkelstein, Herzliya (IL); Ramy Lidor-Hadas, Kfar Saba (IL); Judith Aronhime, Rehovot (IL)

(73) Assignee: Teva Pharmaceutical Industries, Ltd., Tiqva (IL)

( * ) Notice: Subject to any disclaimer, the term of this patent is extended or adjusted under 35 U.S.C. 154(b) by 0 days.

(21) Appl. No.: 09/898,756

(22) Filed: Jul. 3, 2001

(65) Prior Publication Data

US 2003/0065214 A1 Apr. 3, 2003

Related U.S. Application Data

(63) Continuation of application No. 09/384,145, filed on Aug. 27, 1999, now Pat. No. 6,281,381.

(51) Int. Cl.[7] .................................................. C07F 9/00
(52) U.S. Cl. ......................................................... 562/13
(58) Field of Search ................................. 562/8, 11, 13

(56) References Cited

U.S. PATENT DOCUMENTS

| 4,407,761 | A | 10/1983 | Blum et al. |
| 4,624,947 | A | 11/1986 | Blum et al. |
| 4,711,880 | A | 12/1987 | Stahl et al. |
| 4,922,007 | A | 5/1990 | Kieczykowski et al. |
| 5,019,651 | A | 5/1991 | Kieczykowski |

FOREIGN PATENT DOCUMENTS

| WO | 96/39149 | 12/1996 |
| WO | WO96/39410 | 12/1996 |

OTHER PUBLICATIONS

Chem. abstr., vol. 125, No. 23, Dec. 2, 1996 (Columbus OH, USA), p. 1, col. 2, the abstract No. 291993b, Johnson, K.P., et al., 'Management of Relapsing/Remitting Multiple Sclerosis with Copolymer 1 (Copaxone).' Mult. Scler. 1996, 1(6), 325–326 (Eng.), see entire document.

CA:83:147667 abs of Biopolymers by Murphy 14(7) pp. 1487–1501.

CA:90:95900 abs of Dokl, Akad, Nauk Az. SSR by Dikareva 34(8) pp. 41–45.

*Primary Examiner*—Jean F. Vollano
(74) *Attorney, Agent, or Firm*—Kenyon & Kenyon

(57) ABSTRACT

New hydrate forms of alendronate sodium, having water content of between about one and about twelve percent, and processes for their manufacture, are disclosed. New crystalline forms of alendronate sodium B, D, E, F, G and H, and processes for manufacturing them, are also disclosed. These new forms of alendronate sodium are suitable for incorporation into pharmaceutical compositions for combating bone resorption in bone diseases.

37 Claims, 24 Drawing Sheets

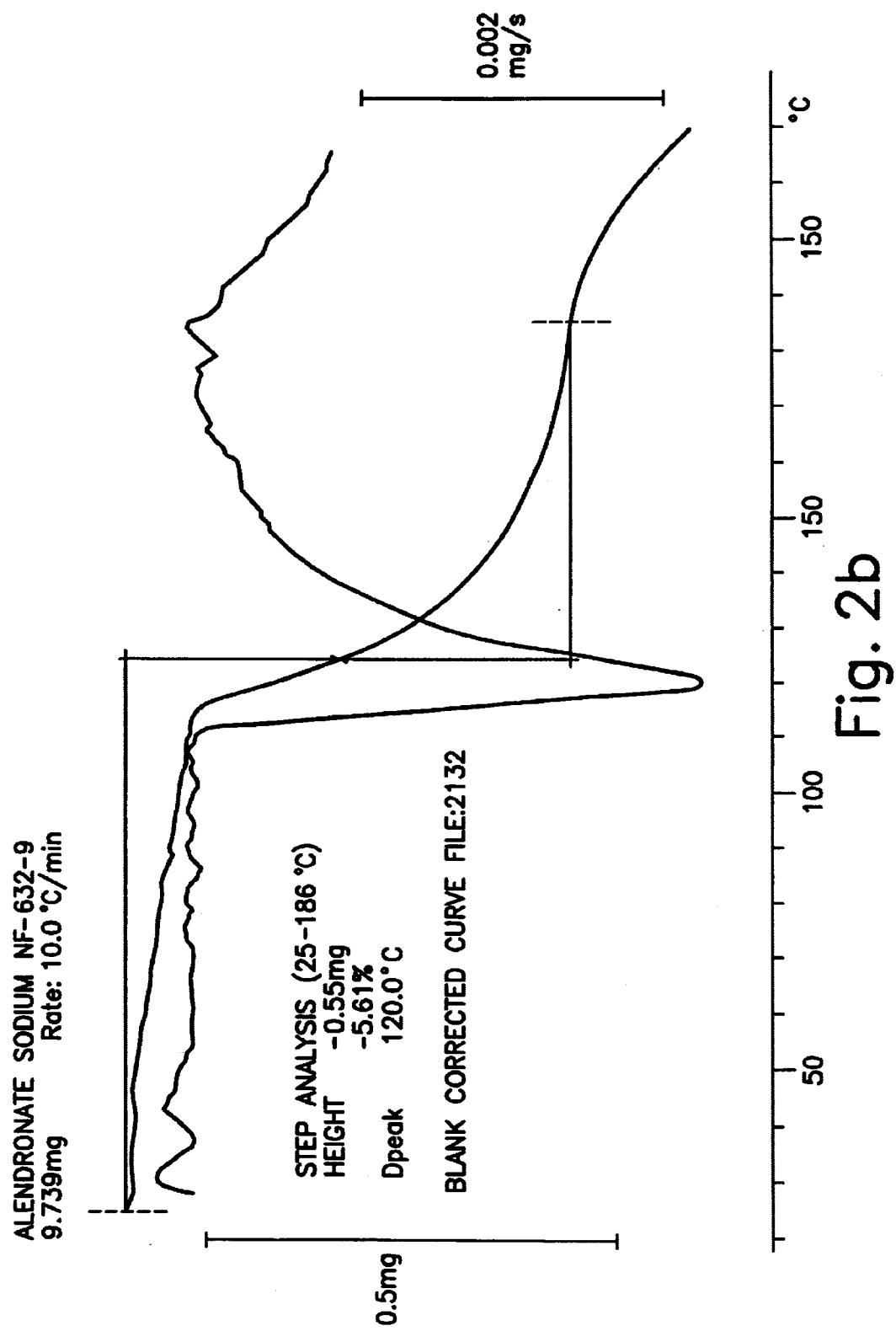

HYDRATE FORMS OF ALENDRONATE SODIUM, PROCESSES FOR MANUFACTURE THEREOF, AND PHARMACEUTICAL COMPOSITIONS THEREOF

This application is a continuation of application Ser. No. 09/384,145 filed Aug. 27, 1999, now U.S. Pat No. 6,281,381.

FIELD OF THE INVENTION

This invention relates to new hydrate and crystalline forms of alendronate sodium, processes for the manufacture thereof, and pharmaceutical compositions thereof.

BACKGROUND OF THE INVENTION

Alendronate sodium, the sodium salt of alendronic acid, also known as 4-amino-1-hydroxybutylidene-1,1-bisphosphonic acid monosodium, has the formula I:

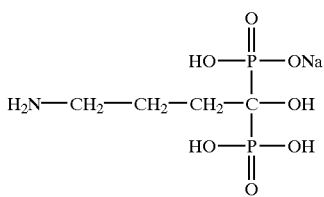

(I)

It is an agent for combating bone resorption in bone diseases including osteoporosis and Paget's disease.

Various methods for preparing alendronic acid are known in the art and have been disclosed in M. I. Kabachnik et al., Synthesis and Acid-Base and Complexing Properties of Amino-Substituted α-Hydroxyalkylidene-diphosphonic Acids, Izv. Akad. Nauk USSR, Ser. Khim, 2,433 (1978) and in U.S. Pat. Nos. 4,407,761, 4,621,077, 4,705,651, 5,039,819 and 5,159,108.

U.S. Pat. No. 4,922,007 describes the preparation of a trihydrate of alendronate sodium by reaction of 4-aminobutyric acid with phosphorous acid and phosphorous trichloride in the presence of methanesulfonic acid followed by the addition of sodium hydroxide.

The present invention provides new forms of alendronate sodium, having water content of 1.3 to 11.7 percent, and processes for their manufacture. Moreover, the present invention provides new crystalline forms of alendronate sodium, designated forms B, D, E, F, G and H, and processes for the manufacture thereof.

OBJECTS AND SUMMARY OF THE INVENTION

The present invention provides novel hydrate forms of alendronate sodium having water content of between 1.3 and 11.7 percent water. Typically, but without limitation, the present invention relates to the following novel hydrate forms of alendronate monosodium: 1/4 hydrate, 1/3 hydrate, hemihydrate, 2/3 hydrate, 3/4 hydrate, monohydrate, 5/4 hydrate, 4/3 hydrate, 3/2 hydrate, 5/3 hydrate, 7/4 hydrate and dihydrate.

The present invention provides a new crystalline Form B of alendronate sodium, having a powder X-ray diffractogram substantially as depicted in FIG. 1a, with characteristic peaks at 12.2±0.2, 13.3±0.2, 14.8±0.2, 15.8±0.2, 16.3±0.2, 16.6±0.2, 17.2±0.2, 19.4±0.2, 21.3±0.2, 22.6±0.2, 23.2±0.2, 24.0±0.2, 25.2±0.2, 25.8±0.2, 27.4±0.2, 29.4±0.2, and 36.0±0.2 degrees 2 theta. Alendronate sodium Form B has significant IR bands as depicted in FIG. 1c at 654 cm$^{-1}$, 955 cm$^{-1}$, 1074 cm-1, 1261 cm$^{-1}$, 1309 cm$^{-1}$, and 1614 cm$^{-1}$. The TGA curve, FIG. 1b, shows a clear two-step loss on drying of 7.2%, which implies that the crystal form B contains a stoichiometric quantity of water close to that of the monohydrate (expected loss on drying value: 6.2%).

Another embodiment of the invention is a new crystalline Form D of alendronate sodium, having a powder X-ray diffractogram substantially as depicted in FIG. 4a, with characteristic peaks at 13.1±0.2, 15.2±0.2, 16.3±0.2, 18.4±0.2, 20.8±0.2, 22.3±0.2, 22.5±0.2, 23.4±0.2, 23.7±0.2, 31.4±0.2, and 35.7±0.2 degrees 2 theta. Form D as depicted in FIG. 4c has significant IR bands at 662 cm$^{-1}$, 919 cm$^{-1}$, 934 cm$^{-1}$, 954 cm$^{-1}$, 1054 cm$^{-1}$, 1072 cm$^{-1}$ 1297 cm$^{-1}$ and 1318 cm$^{-1}$. The TGA curve, as depicted in FIG. 4b, shows a gradual loss on drying of 4.1% up to 180° C.

An additional embodiment is a new crystalline Form E of alendronate sodium, having a powder X-ray diffractogram substantially as depicted in FIG. 5a, with characteristic peaks at 7.0±0.2, 9.3±0.2, 11.8±0.2, 13.3±0.2, 14.0±0.2, 15.3±0.2, 16.2±0.2, 19.4±0.2 degrees 2 theta. Form E has significant IR bands as depicted in FIG. 5c at 660 cm$^{-1}$, 897 cm$^{-1}$, 924 cm$^{-1}$, 953 cm$^{-1}$, 970 cm$^{-1}$, 1017 cm$^{-1}$, 1040 cm$^{-1}$, 1093 cm$^{-1}$ 1149 cm$^{-1}$, 1177 cm$^{-1}$, 1252 cm$^{-1}$ 1293 cm$^{-1}$ 1337 cm$^{-1}$, 1535 cm$^{-1}$, 1606 cm$^{-1}$, and 1639 cm$^{-1}$. The TGA curve, as depicted in FIG. 5b, shows a gradual loss on drying of 3.7% up to 150° C.

A still further embodiment of the invention is a new crystalline Form F of alendronate sodium, having a powder X-ray diffractogram substantially as depicted in FIG. 6a, with characteristic peaks at 9.3±0.2, 11.7±0.2, 13.0±0.2, 13.4±0.2, 14.2±0.2, 15.3±0.2, 16.2±0.2, 17.4±0.2, 19.1±0.2, 19.4±0.2 and 25.5±0.2 degrees 2 theta. Form F has significant IR bands as depicted in FIG. 6c at 660 cm$^{-1}$, 893 cm$^{-1}$, 930 cm$^{-1}$, 953 cm$^{-1}$, 970 cm$^{-1}$, 982 cm$^{-1}$, 1010 cm$^{-1}$, 1033 cm$^{-1}$ 1052 cm$^{-1}$, 1060 cm$^{-1}$, 1069 cm$^{-1}$, 1109 cm$^{-1}$ and 1169 cm$^{-1}$, 1251 cm$^{-1}$, 1338 cm$^{-1}$, 1498 cm$^{-1}$, 1544 cm$^{-1}$, 1603 cm$^{-1}$, 1637 cm$^{-1}$, 1664 cm$^{-1}$. The TGA FIG. 6b curve shows a gradual loss on drying of 1.3% up to 150° C.

A further embodiment is a new crystalline Form G of alendronate sodium, having a powder X-ray diffractogram substantially as depicted in FIG. 7a, with characteristic peaks at 9.5±0.2, 10.1±0.2, 12.7±0.2, 16.2±0.2, 17.3±0.2, 17.6±0.2, 19.1±0.2, 20.4±0.2, 20.9±0.2, 22.1±0.2, 24.8±0.2, 25.5±0.2, 28.0±0.2, 29.0±0.2, 29.6±0.2, 30.4±0.2, 32.4±0.2, and 32.8±0.2 degrees 2 theta. Form G has significant IR bands as depicted in FIG. 7c at 665 cm$^{-1}$, 751 cm$^{-1}$, 856 cm$^{-1}$, 895 cm$^{-1}$, 913 cm$^{-1}$, 939 cm$^{-1}$, 1011 cm$^{-1}$, 1021 cm$^{-1}$, 1050 cm$^{-1}$, 1091 cm$^{-1}$, 1155 cm$^{-1}$, 1273 cm$^{-1}$, 1305 cm$^{-1}$, 1337 cm$^{-1}$, 1510 cm$^{-1}$, and 1639 cm$^{-1}$. The TGA curve, FIG. 7b, shows a loss on drying of 6.5% which indicates that the crystal form G contains a stoichiometric quantity of water corresponding to that of the monohydrate (expected loss on drying value: 6.2%). This TGA step is sharp and occurs at 195° C. The relatively high temperature of dehydration implies that the water is bound tightly to the alendronate molecule. The dehydration step is immediately followed by another step due to decomposition. Due to the decomposition process that occurs adjacent to the dehydration, the conventional loss of drying method is not feasible, and for loss on drying determination the TGA is used.

Yet another embodiment is a new crystalline Form H of alendronate sodium, having a powder X-ray diffractogram substantially as depicted in FIG. 8a, with characteristic peaks at 9.2±0.2, 13.0±0.2, 14.2±0.2, 15.0±0.2, 17.1±0.2, 20.7±0.2, 22.0±0.2, 22.4±0.2, degrees two theta. Form H has significant IR bands, as depicted in FIG. 8c, of 664 cm$^{-1}$, 688 cm$^{-1}$, 722 cm$^{-1}$, 751 cm$^{-1}$, 863 cm$^{-1}$, 893 cm$^{-1}$, 918 cm$^{-1}$, 936 cm$^{-1}$, 984 cm$^{-1}$, 1010 cm$^{-1}$, 1036 cm$^{-1}$, 1052 cm$^{-1}$, 1092 cm$^{-1}$, 1157 cm$^{-1}$, 1273 cm$^{-1}$, 1303 cm$^{-1}$ and 1338 cm$^{-1}$, 1499 cm$^{-1}$, 1598 cm$^{-1}$, 1636 cm$^{-1}$, and 1664 cm$^{-1}$. The TGA curve FIG. 8b shows a sharp loss on drying of 3.7% at 170° C.

All of sodium alendronate crystalline forms B, D, E, F, G and H contain water in the amount of 2.2 to 9.0% by weight.

The invention further provides a new hydrate form of alendronate sodium having a water content of 1.3% to 3.1%.

A further embodiment is a new hydrate form of alendronate sodium having a water content of 2.5% to 3.5%.

A further embodiment is a new hydrate form of alendronate sodium having a water content of 2.8% to 3.9%.

An additional embodiment is a new hydrate form of alendronate sodium having a water content of 3.2% to 5.8%.

Another embodiment is a new hydrate form of alendronate sodium having a water content of 5.1% to 7.0%.

A still further embodiment is a new hydrate form of alendronate sodium having a water content of 6.4% to 9.0%.

The invention also provides a new crystalline Form B of alendronate sodium, having a water content of 6.4% to 9.0%.

The invention further provides a new crystalline Form D of alendronate sodium, having a water content of 3.2% to 5.8%.

The invention further provides a new crystalline Form F of alendronate sodium, having a water content of 1.3% to 3.1%.

The invention further provides a new crystalline Form G of alendronate sodium, having a water content of 5.1% to 7.0%.

The invention further provides a new crystalline Form E of alendronate sodium, having a water content of 2.8% to 3.9%.

The invention further provides a new crystalline Form H of alendronate sodium, having a water content of 2.5% to 3.7%.

The invention provides a new monohydrate and a new dehydrate of alendronate sodium, having an X-ray diffractogram substantially as depicted in FIGS. 2a and 3a, accordingly, with characteristic peaks at 9.3±0.2, 12.4±0.2, 13.5±0.2, 17.1±0.2, 18.5±0.2, 19.7±0.2, 20.3±0.2, 21.0±0.2, 21.8±0.2, 23.4±0.2, 24.3±0.2, 24.9±0.2, 26.3±0.2, 30.0±0.2, and 34.4±0.2 degrees 2 theta. Form C as depicted in FIGS. 2b and 3b has significant IR bands at 660 cm$^{-1}$, 745 cm$^{-1}$, 865 cm$^{-1}$, 913 cm$^{-1}$, 952 cm$^{-1}$, 966 cm$^{-1}$, 1017 cm$^{-1}$, 1046 cm$^{-1}$, 1128 cm$^{-1}$, 1174 cm$^{-1}$, 1235 cm$^{-1}$, 1340 cm$^{-1}$, 1402 cm$^{-1}$, 1544 cm$^{-1}$, 1606 cm$^{-1}$, and 1644 cm$^{-1}$. The TGA curve of the monohydrate Form C (FIG. 2b) shows a loss on drying of 5.6% which implies that the crystal Form C contains a stoichiometric quantity of water close to that of the monohydrate (expected loss on drying value: 6.2%). The TGA curve of the dehydrate Form C (FIG. 3b) shows a sharp C loss on drying of 12.0% which implies that the crystal Form C contains a stoichiometric quantity of water corresponding to dehydrate (expected loss on drying value: 11.7%).

The present invention also relates to the method of preparing the compound 4-amino-1-hydroxybutylidene-1, 1-bisphosphonic acid monosodium salt having water content of 1.3% to 11.7% by reacting alendronic acid with one equivalent of sodium base in an aqueous organic solvent selected from the group consisting of. acetone, DMSO, DMF, acetonitrile, alcohols, polyalcohols and/or their ethers, pyridine, sulfolane, -methyl pyrrolidinone and dioxane.

The invention further provides a method for making Form D of alendronate sodium, comprising treating alendronic acid anhydrous in a lower alkanol with 1 equivalent of sodium base and 0 to 4 equivalents of water, followed by isolating the crystalline alendronate sodium Form D.

The invention further provides a method for making Form E of alendronate sodium, comprising treating alendronic acid, which is in anhydrous or monohydrate form, in a lower alkanol with 1 equivalent of sodium base and 9 to 15 equivalents of water, followed by isolating the crystalline alendronate sodium Form E.

The invention further provides a method for making Form F of alendronate sodium, comprising treating alendronic acid, in a lower alkanol with 1 equivalent of sodium base and 5 to 8 equivalents of water for anhydrous form and 3 to 20 equivalents of water for monohydrate form, followed by isolating the crystalline alendronate sodium Form F.

The invention further provides a method for making alendronate sodium monohydrate, comprising treating alendronic acid, in a lower alkanol with 1 equivalent of sodium base and water under the conditions described hereinafter, followed by isolating the alendronate sodium monohydrate.

The invention further provides a method for making Form G of alendronate sodium, comprising treating alendronic acid, in a lower alkanol with 1 equivalent of sodium base and water under the conditions described hereinafter, followed by isolating the crystalline alendronate sodium Form G.

Typical but not limiting conditions for preparing alendronate sodium Form G are as described in the following table:

| Starting Alendronic Acid Hydrate Form | Solvent | Preferred Range of Water Equivalent | Range of Water Equivalent |
| --- | --- | --- | --- |
| Monohydrate | Methanol | 20–200 | 40–175 |
| Monohydrate | Ethanol | 15–100 | 20–80 |
| Monohydrate | Isopropanol | 5–40 | 10–20 |
| Anhydrous | Methanol | 50–125 | 80–100 |
| Anhydrous | Ethanol | 15–40 | 25–35 |

The invention further provides a method for making Form G of alendronate sodium comprising treating any one or more of the crystal forms of alendronate sodium selected from the group which consists of Form B, Form C, Form D, Form E, Form F and Form H, in a lower alkanol, preferably ethanol, with 20–40 equivalents of water under the conditions described hereinafter followed by isolating the crystalline alendronate sodium Form G.

The invention further provides a method for making Form G of alendronate sodium comprising treating alendronate monosodium trihydrate in a lower alkanol, preferably ethanol, with 25–35 equivalents of water under the condition described hereinafter, followed by isolating the crystalline alendronate sodium Form G.

The invention further provides a method for making Form G of alendronate sodium comprising treating any one or more forms of alendronate sodium salts preferably selected from the group consisting of monosodium, disodium, trisodium and tetrasodium salts, in a lower alkanol preferably ethanol with 20–40 equivalents of water under the conditions described hereinafter, followed by isolating the crystalline alendronate sodium Form G. In the event that the starting sodium salt is higher than monosodium (e.g. disodium, trisodium or tetrasodium) it is necessary to add an acid, preferably alendronic acid, in order to maintain the pH at about 4.4.

The invention further provides a method for making Form H of alendronate sodium, comprising treating alendronic acid, which is the anhydrous or monohydrate form, in a lower alkanol with one equivalent of sodium base and 25 to 35 equivalents of water, under the conditions described hereinafter, followed by isolating the crystalline alendronate sodium Form H.

The invention further provides a method for making Form B of alendronate sodium, comprising treating alendronic acid monohydrate in a lower alkanol with one equivalent of sodium base and 0 to 4 equivalents of water, followed by obtaining the crystalline alendronate sodium Form B.

The invention further provides a method for making alendronate sodium dihydrate comprising treating crystalline alendronate sodium trihydrate with an effective amount of drying agent followed by isolating the crystalline alendronate sodium dihydrate.

The invention further provides a method for making alendronate sodium monohydrate comprising treating crystalline alendronate sodium trihydrate with a sufficient amount of drying agent followed by isolating the crystalline alendronate sodium monohydrate.

The invention further provides a method for making alendronate sodium monohydrate comprising treating crystalline alendronate sodium dihydrate with a sufficient amount of drying agent followed by isolating the crystalline alendronate sodium monohydrate.

The invention further relates to a pharmaceutical composition which comprises alendronate sodium, having water content of 1.3 to 11.7 percent in a therapeutically effective amount, and a pharmaceutically acceptable carrier.

The invention further relates to a pharmaceutical composition which comprises alendronate sodium in Form B D, E, F, G and/or H in a therapeutically effective amount, and a pharmaceutically acceptable carrier.

BRIEF DESCRIPTION OF THE DRAWINGS

FIGS. 2a, 2b, and 2c show, respectively, the powder X-ray diffraction spectrum, the thermograviometric (TGA) curve and the infrared spectrum of alendronate sodium monohydrate Form C.

DETAILED DESCRIPTION OF THE INVENTION

Figure 1A:
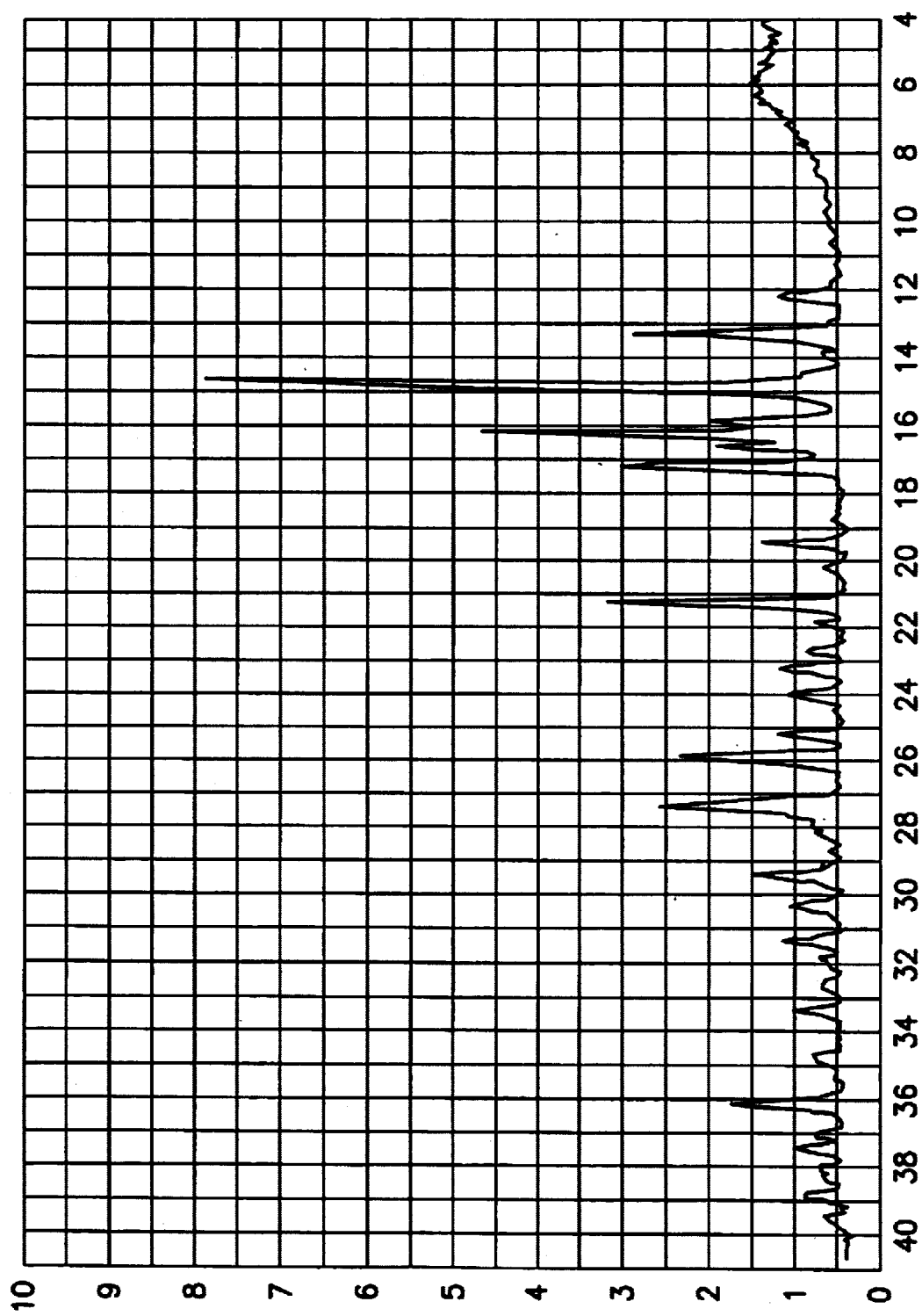
FIGS. 1a, 1b, and 1c show, respectively, the powder X-ray diffraction spectrum, the thermograviometric (TGA) curve and the infrared spectrum of alendronate sodium Form B.
Figure 1B:
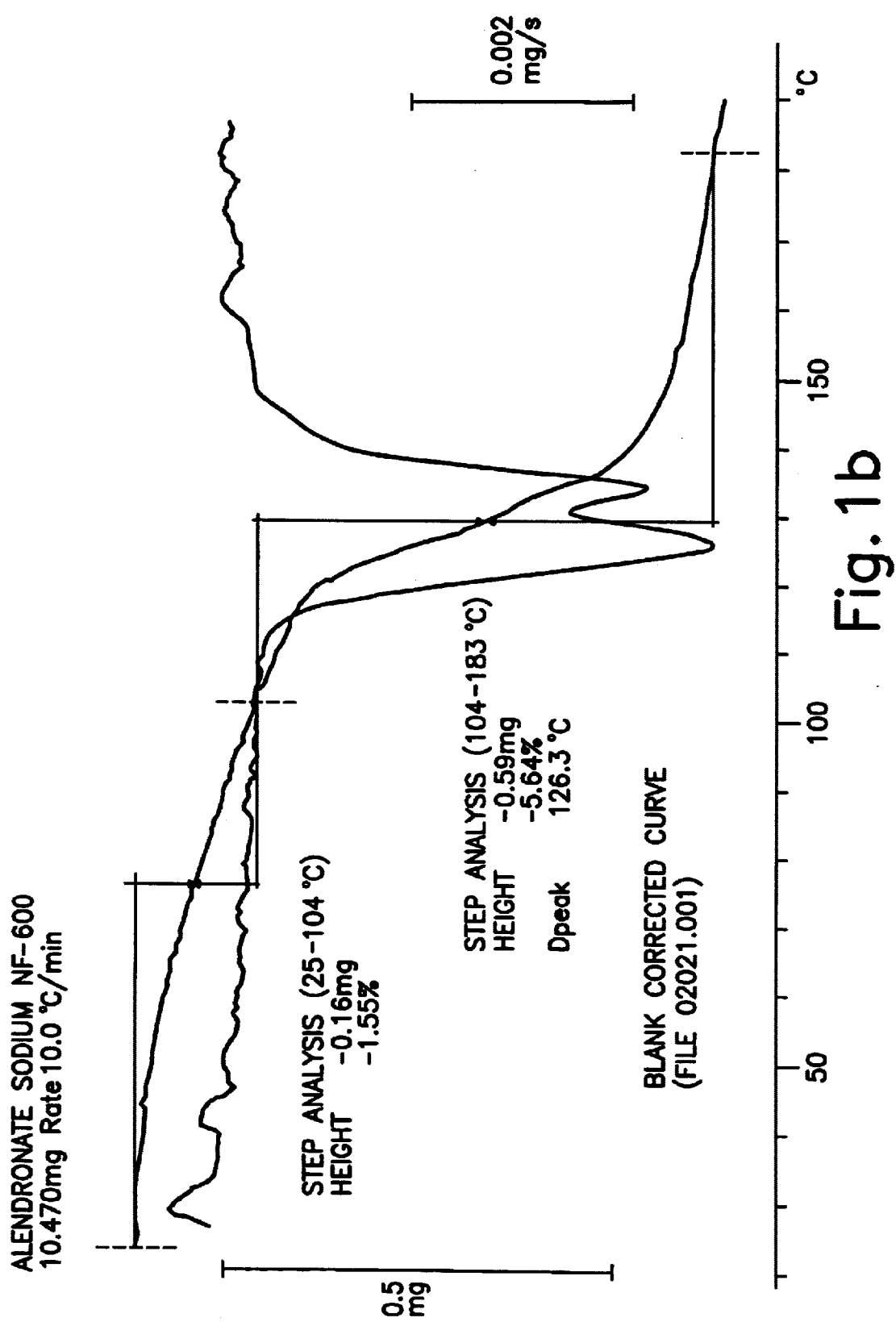
Figure 1C:
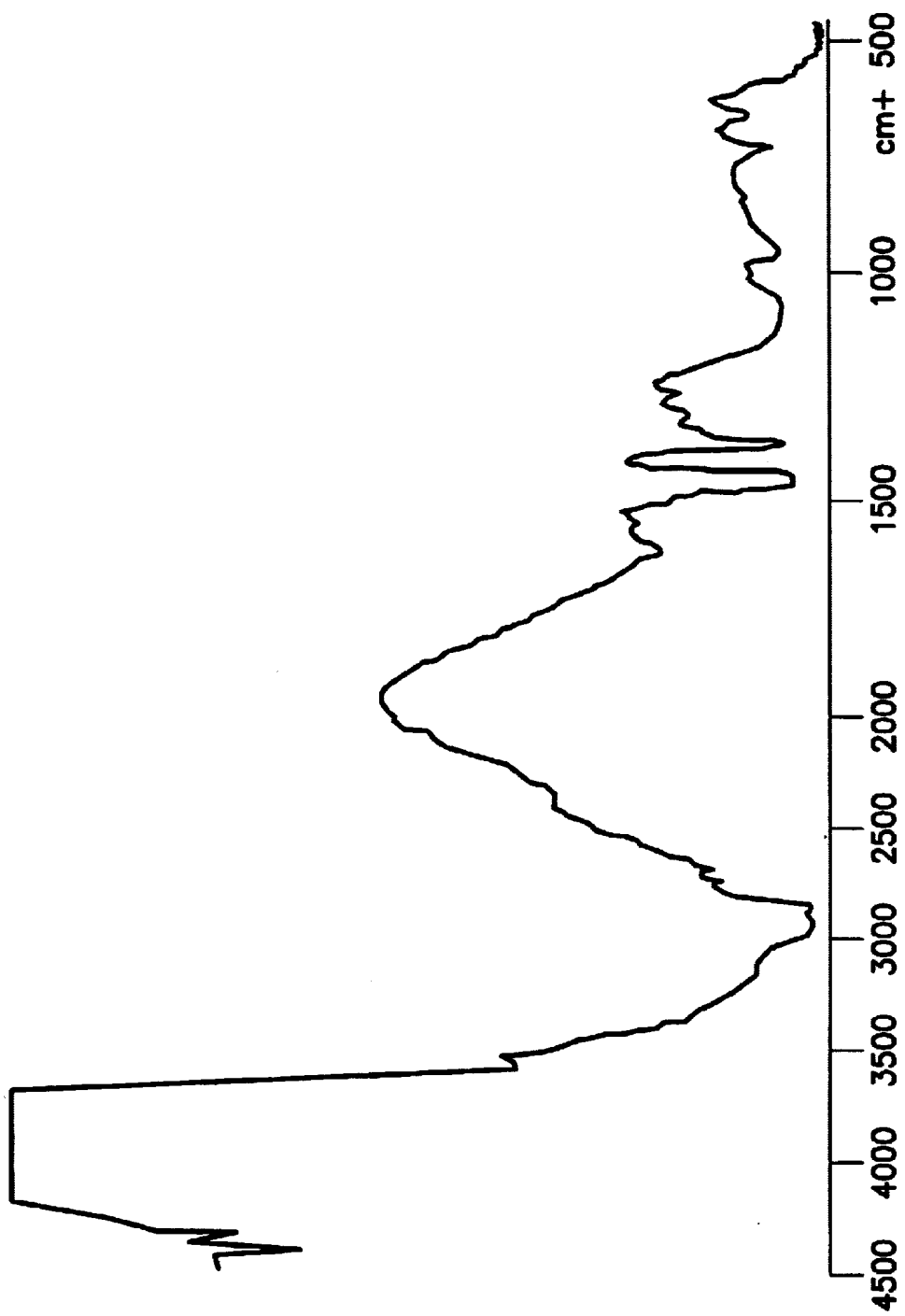
Figure 2A:
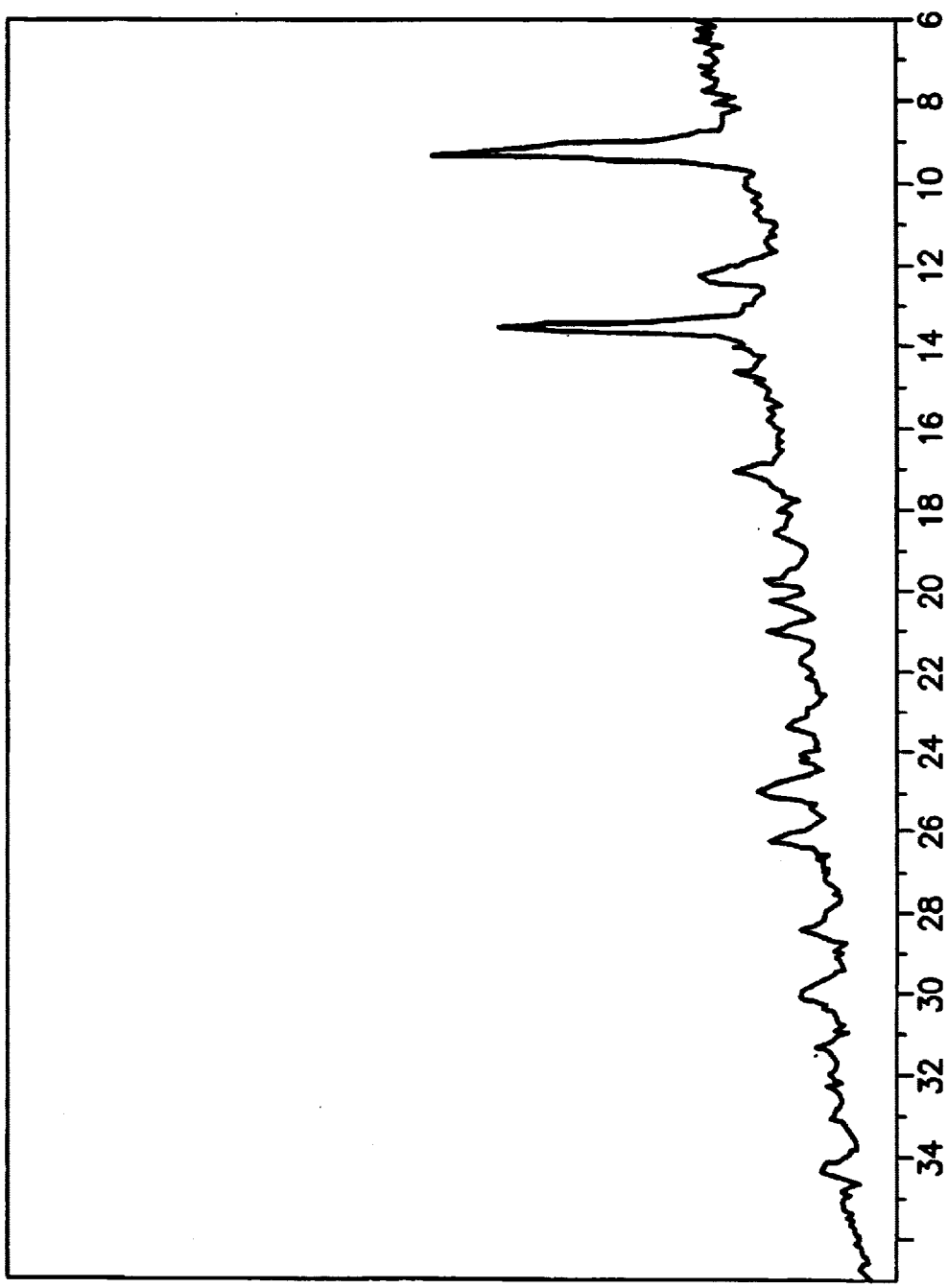
Figure 2C:
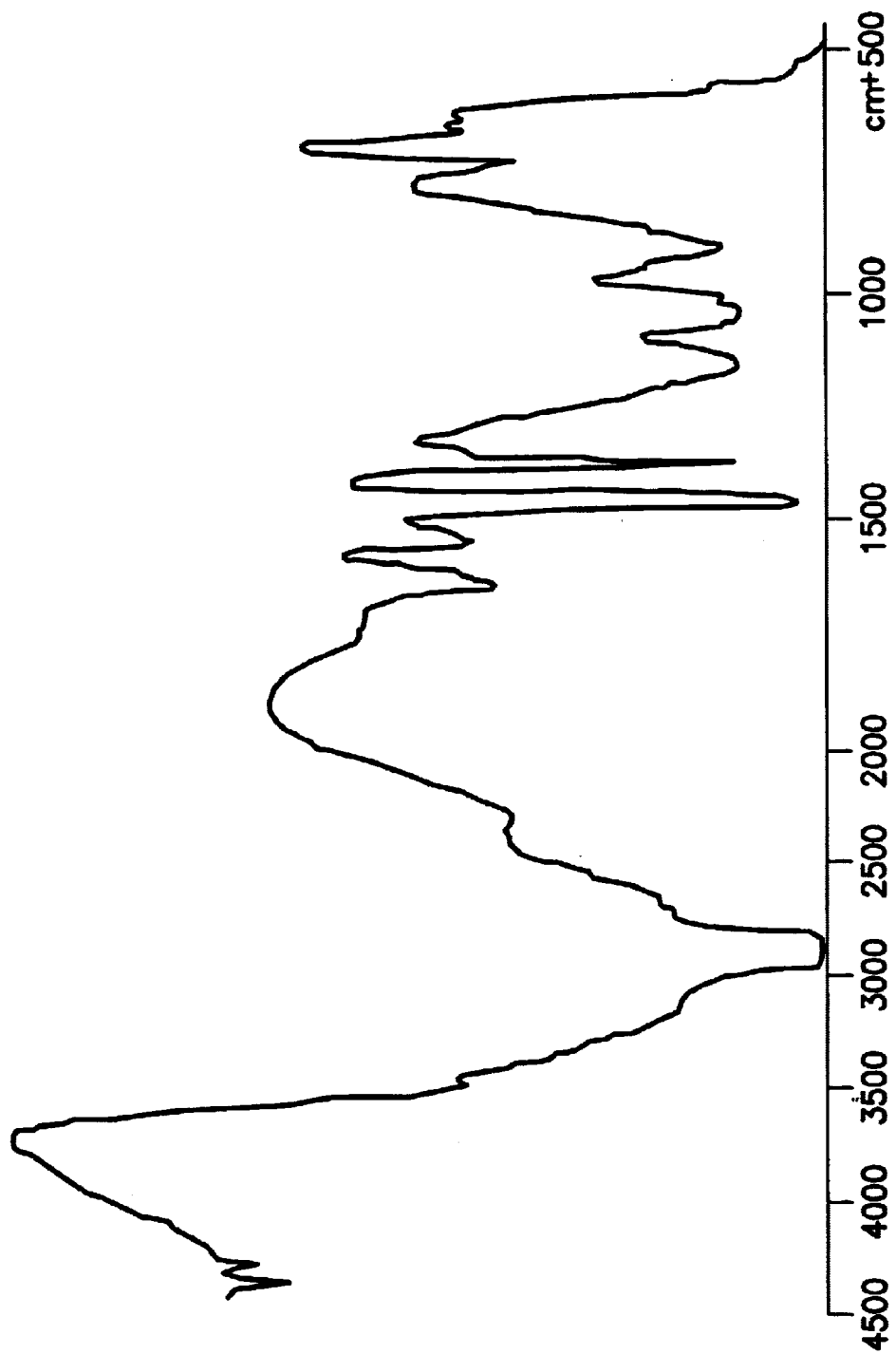
Figure 3A:
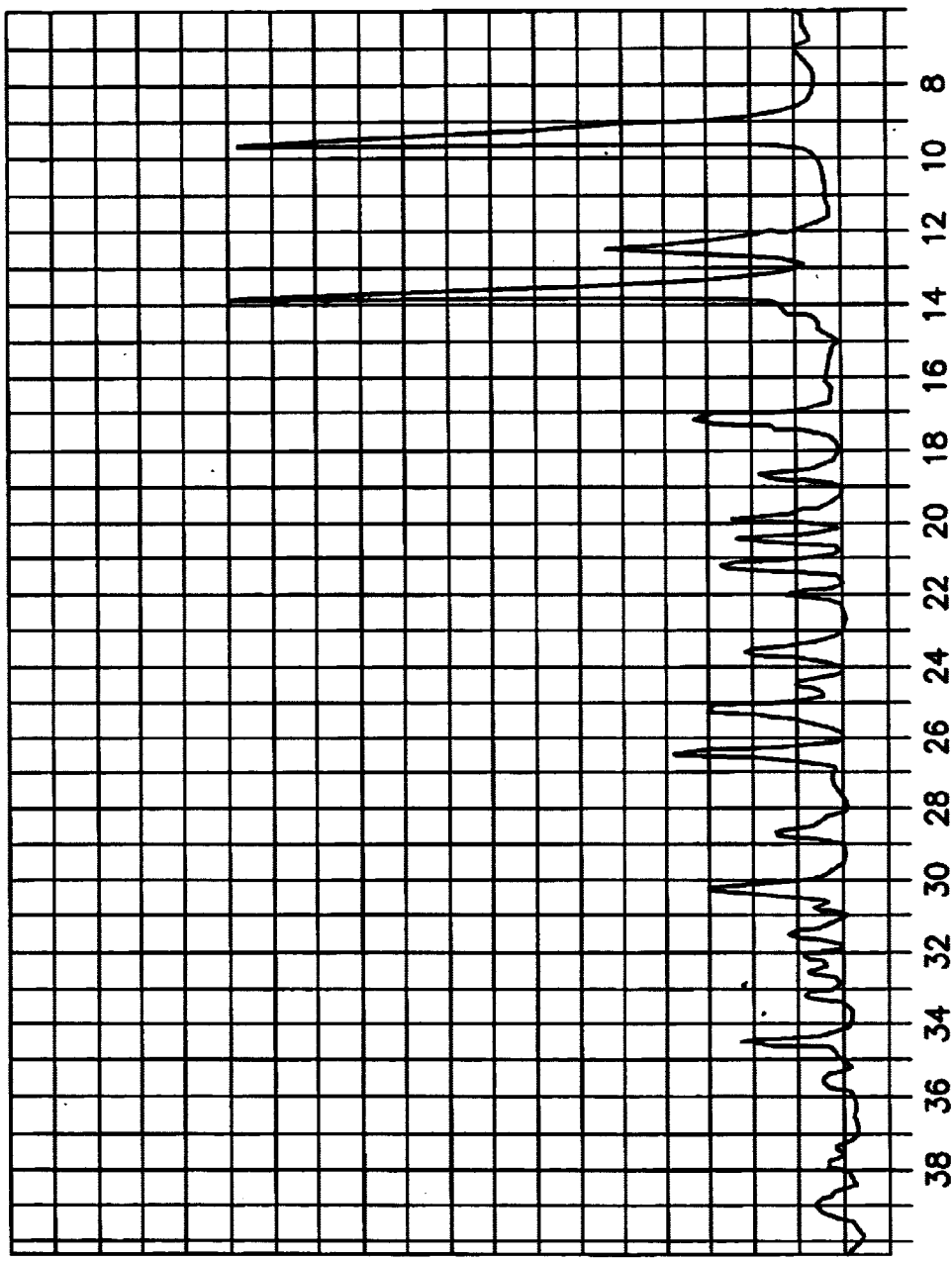
FIGS. 3a, 3b, and 3c show, respectively, the powder X-ray diffraction spectrum, the thermograviometric (TGA) curve and the infrared spectrum of alendronate sodium dihydrate Form C.
Figure 3B:
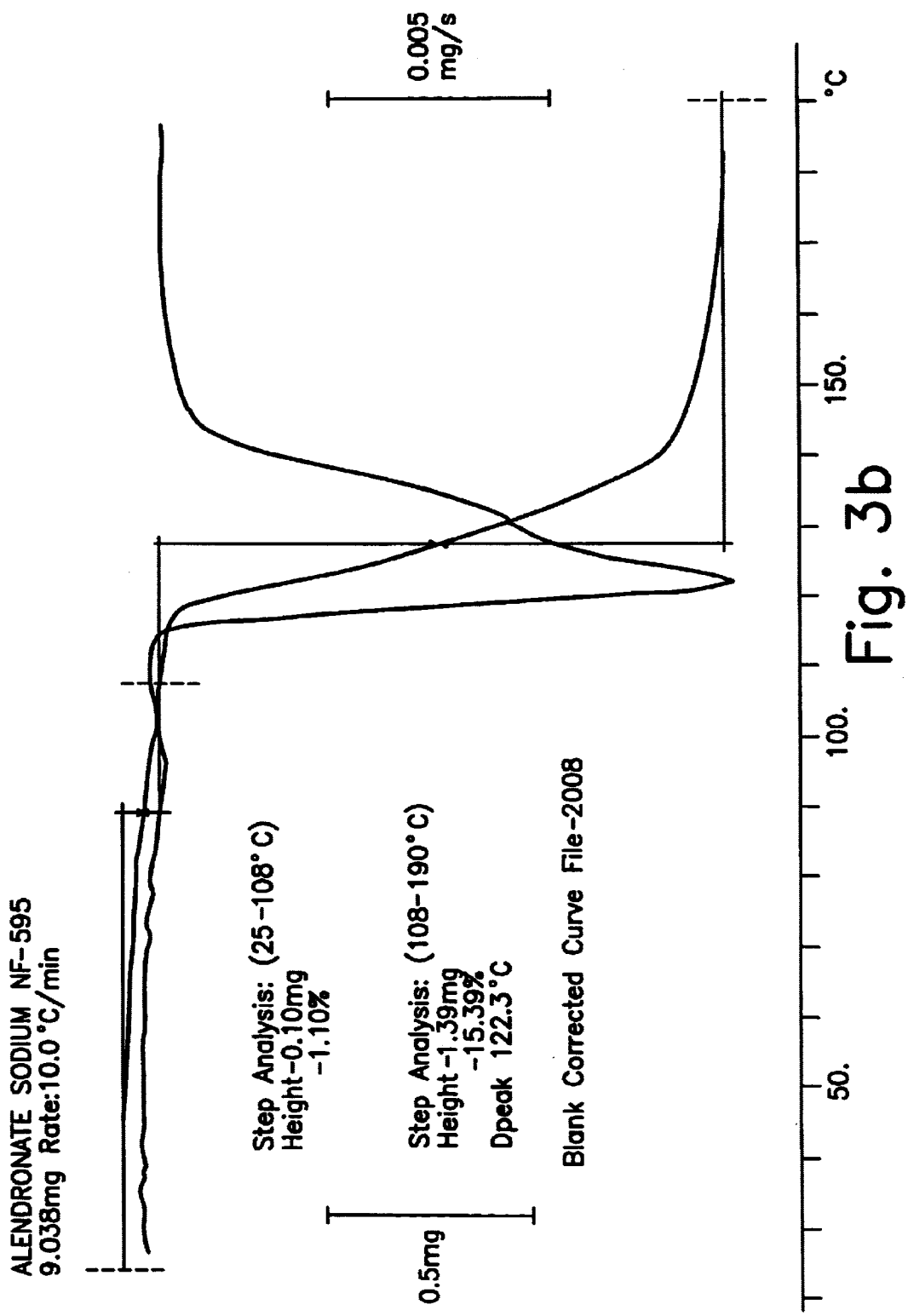
Figure 3C:
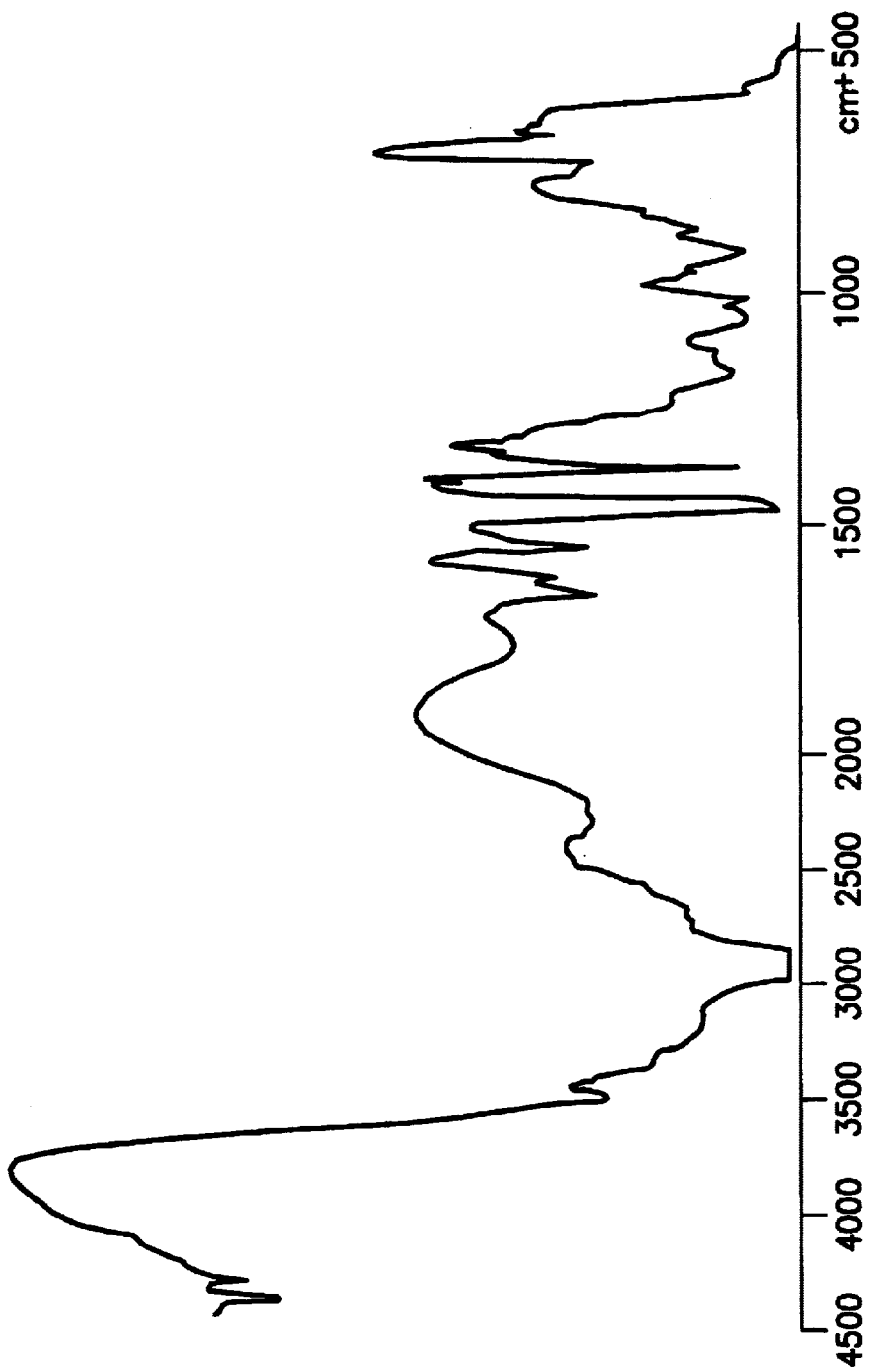
Figure 4A:
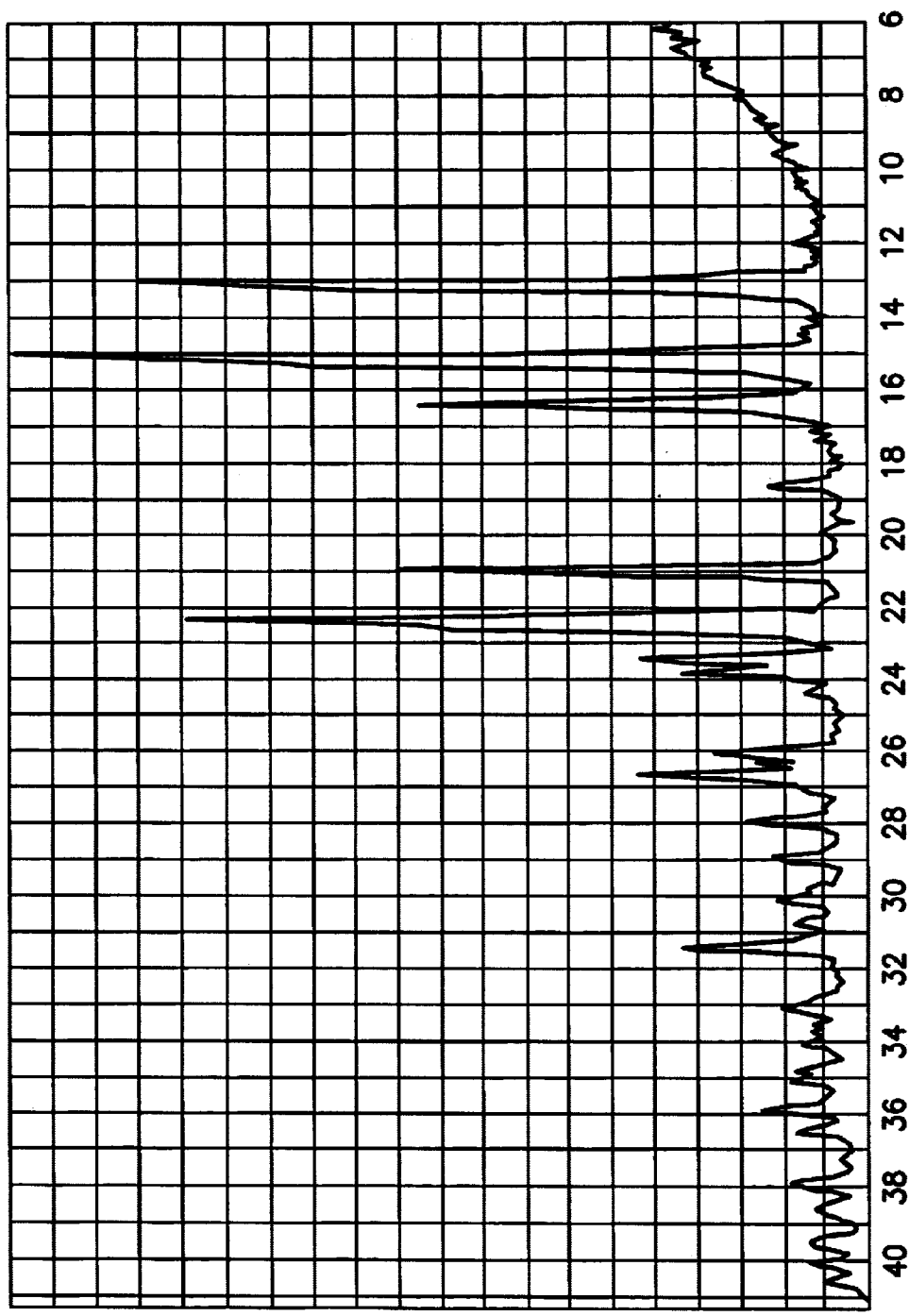
FIGS. 4a, 4b, and 4c show, respectively, the powder X-ray diffraction spectrum, the thermograviometric (TGA) curve and the infrared spectrum of alendronate sodium Form D.
Figure 4B:
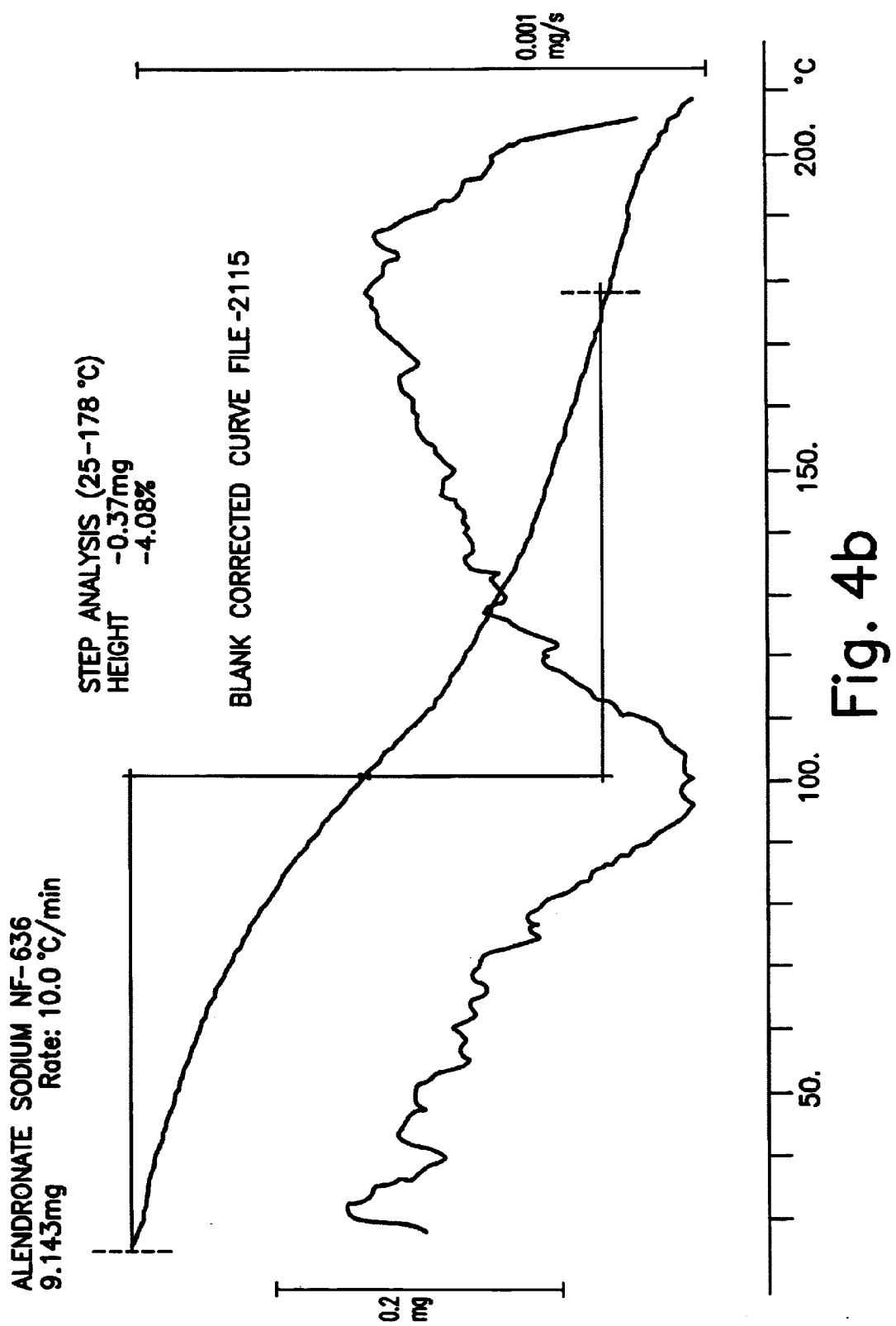
Figure 4C:
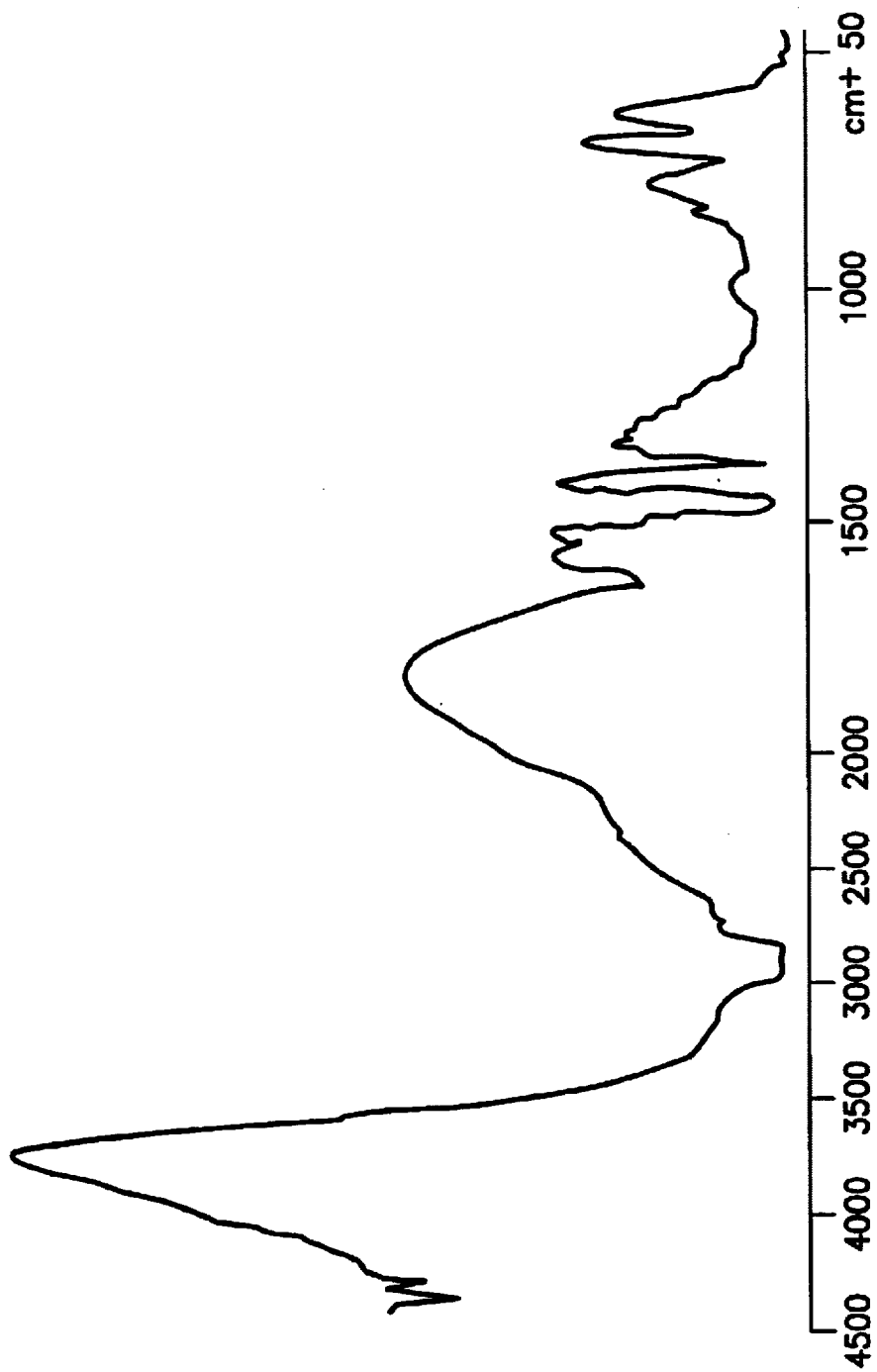
Figure 5A:
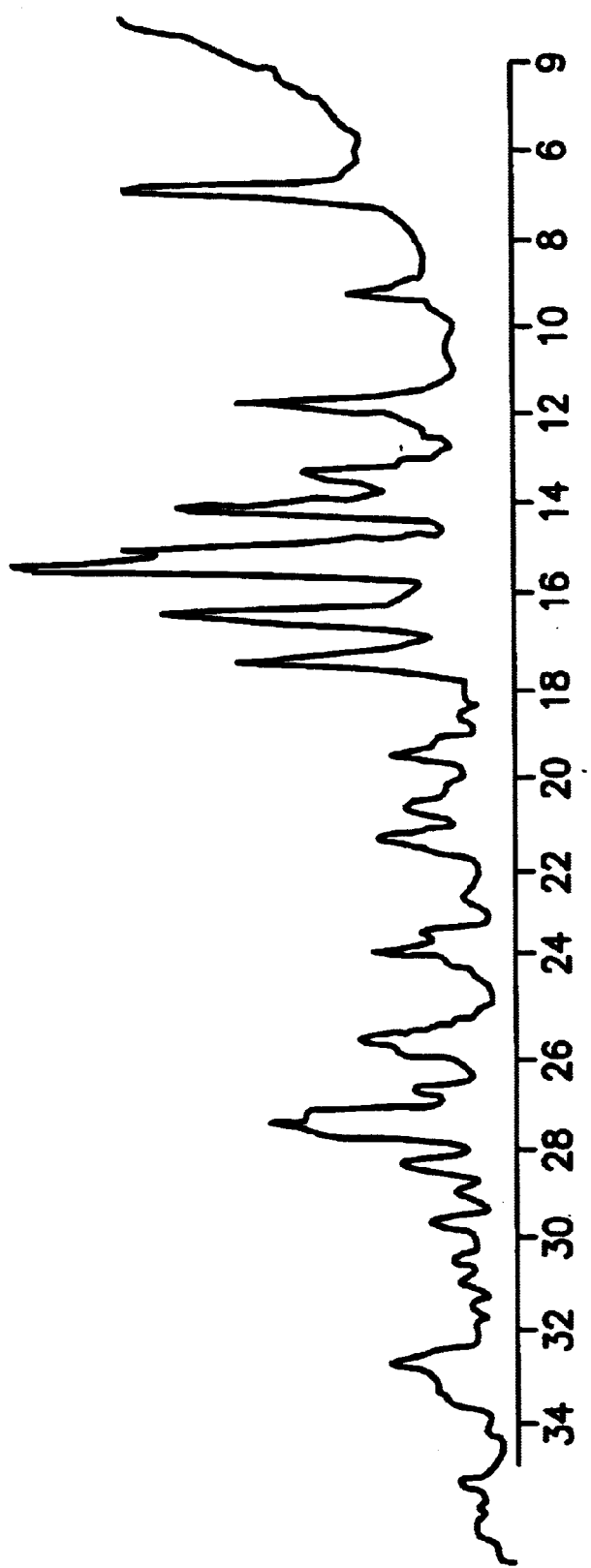
FIGS. 5a, 5b, and 5c show, respectively, the powder X-ray diffraction spectrum, the thermograviometric (TGA) curve and the infrared spectrum of alendronate sodium Form E.
Figure 5B:
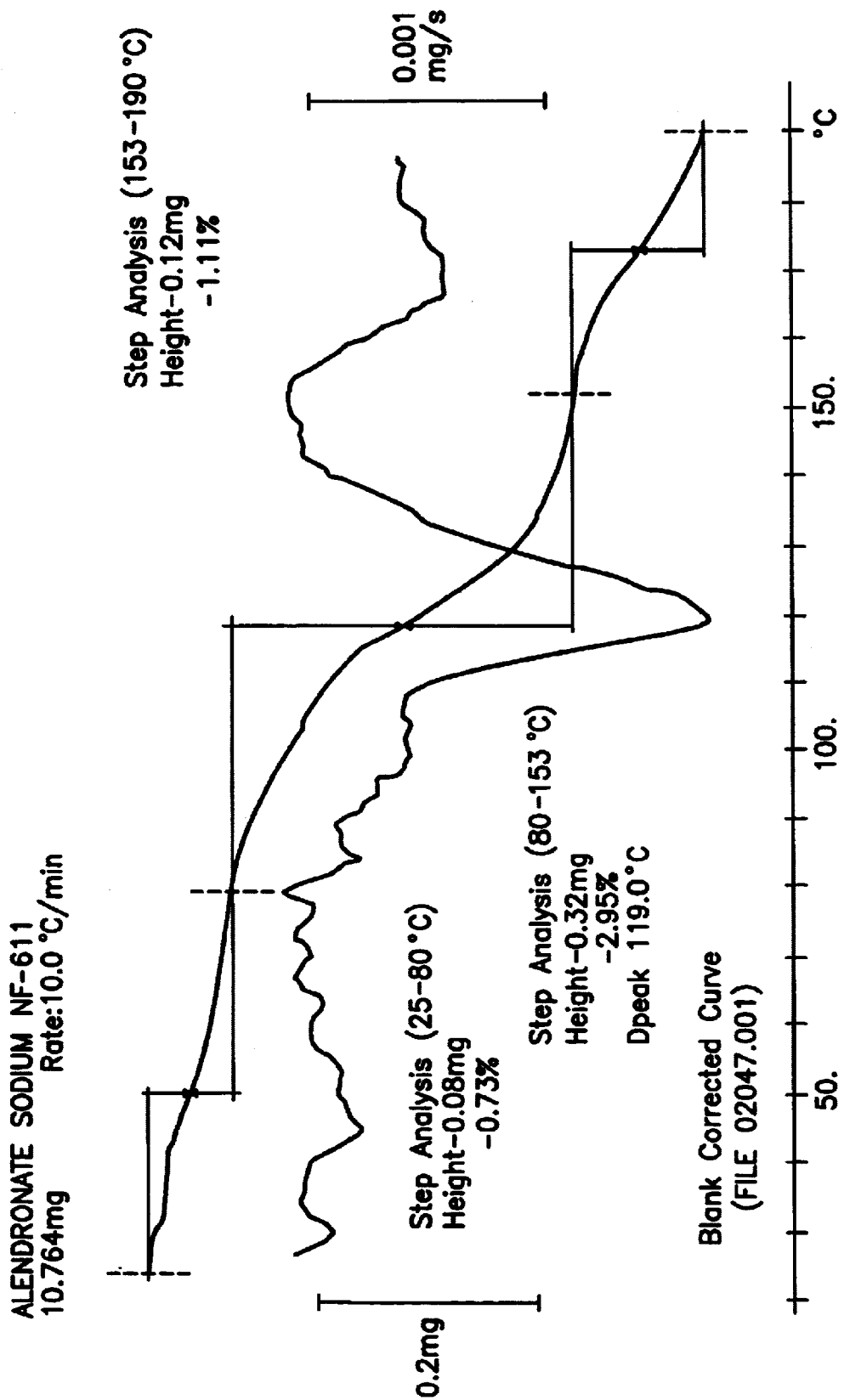
Figure 5C:
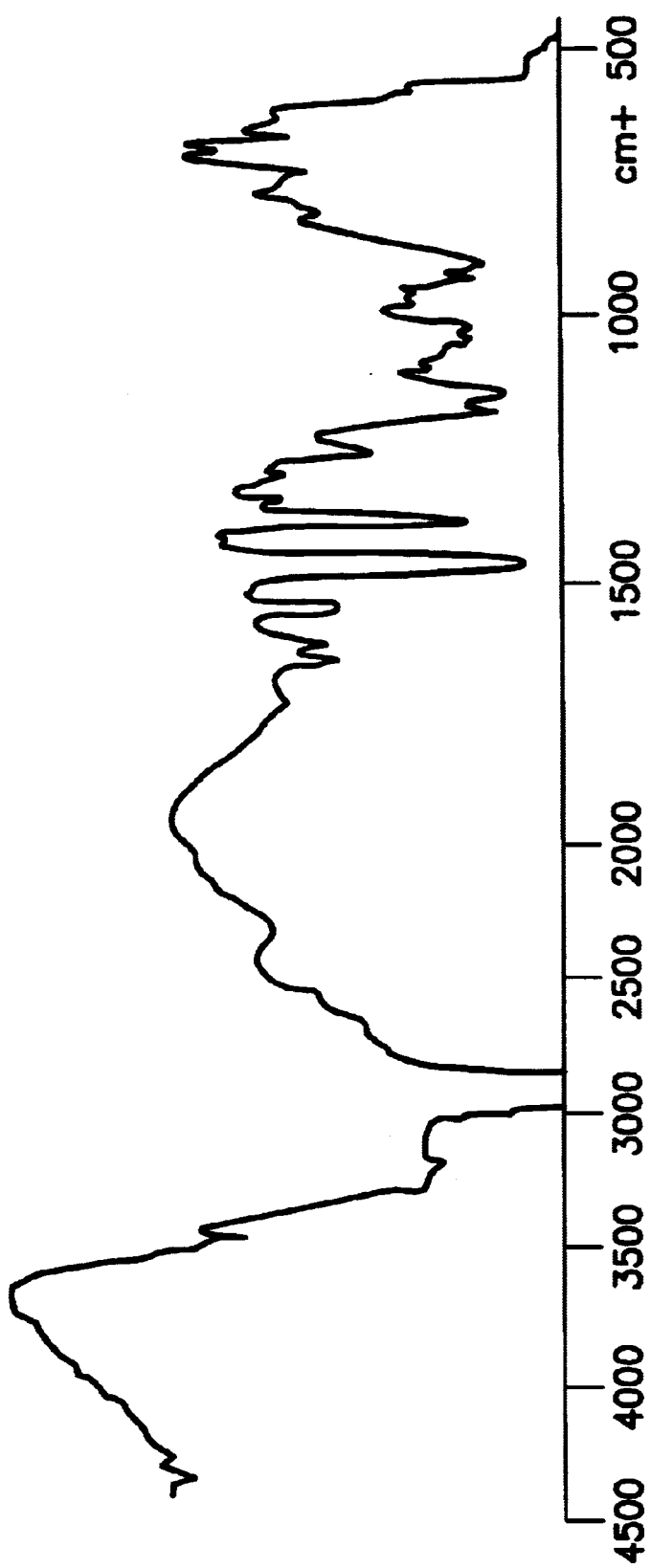
Figure 6A:
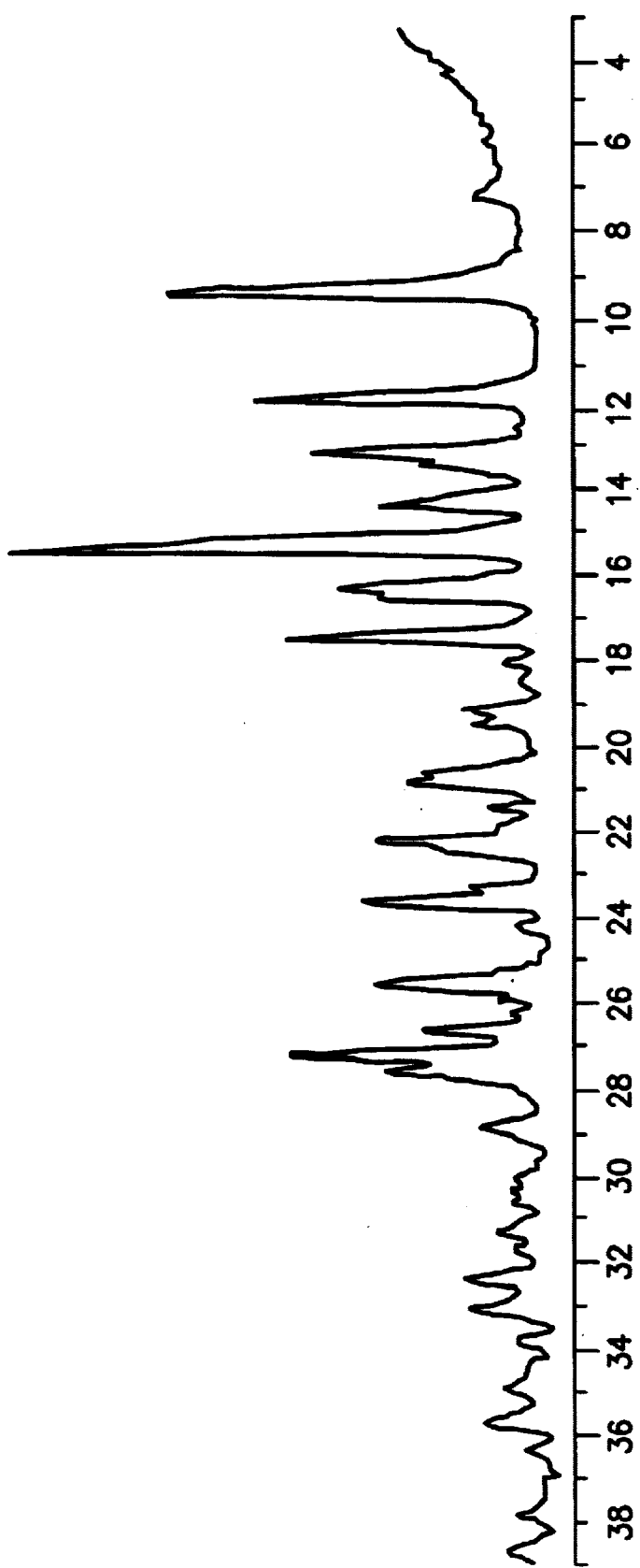
FIGS. 6a, 6b, and 6c show, respectively, the powder X-ray diffraction spectrum, the thermograviometric (TGA) curve and the infrared spectrum of alendronate sodium Form F.
Figure 6B:
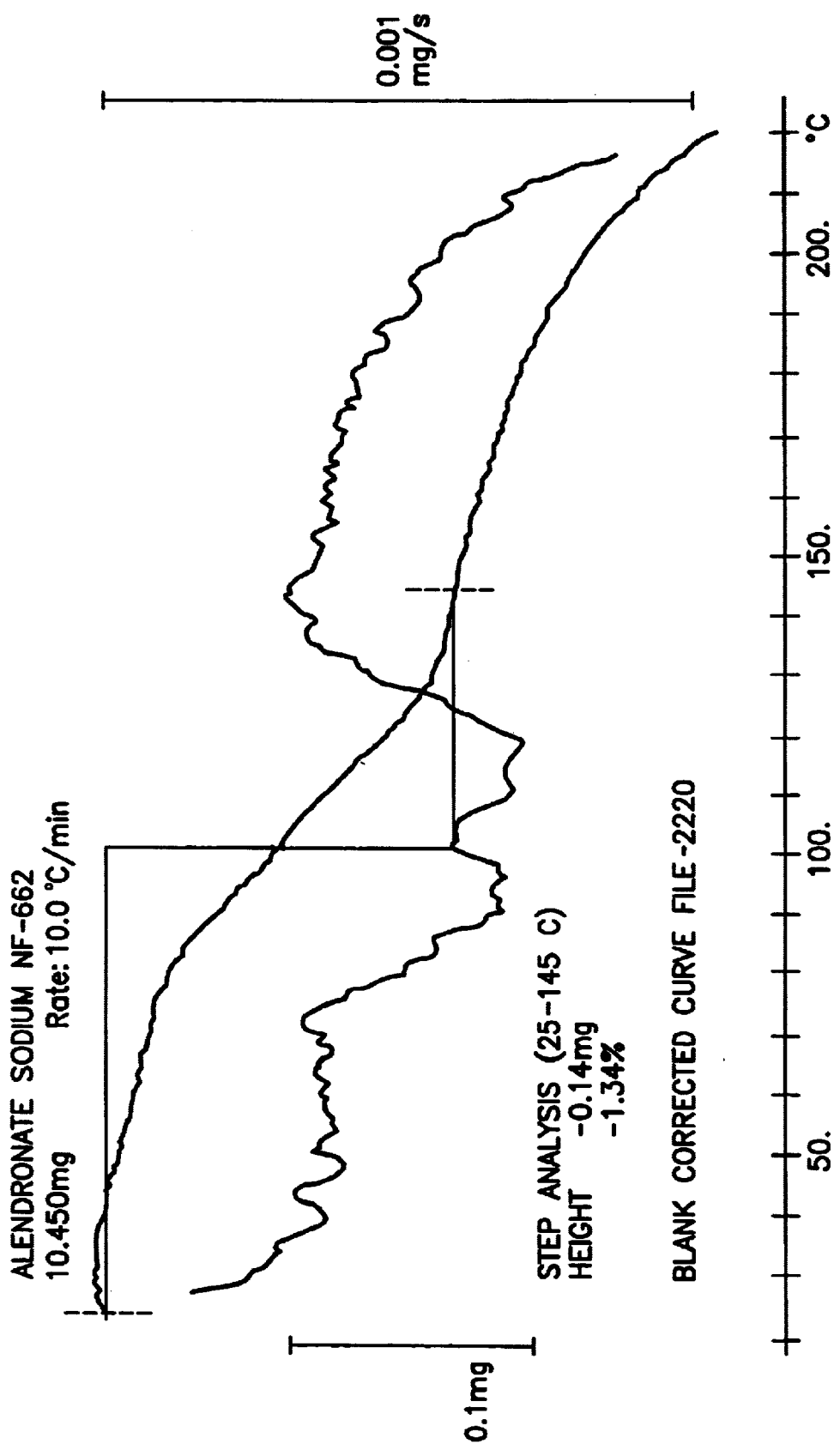
Figure 6C:
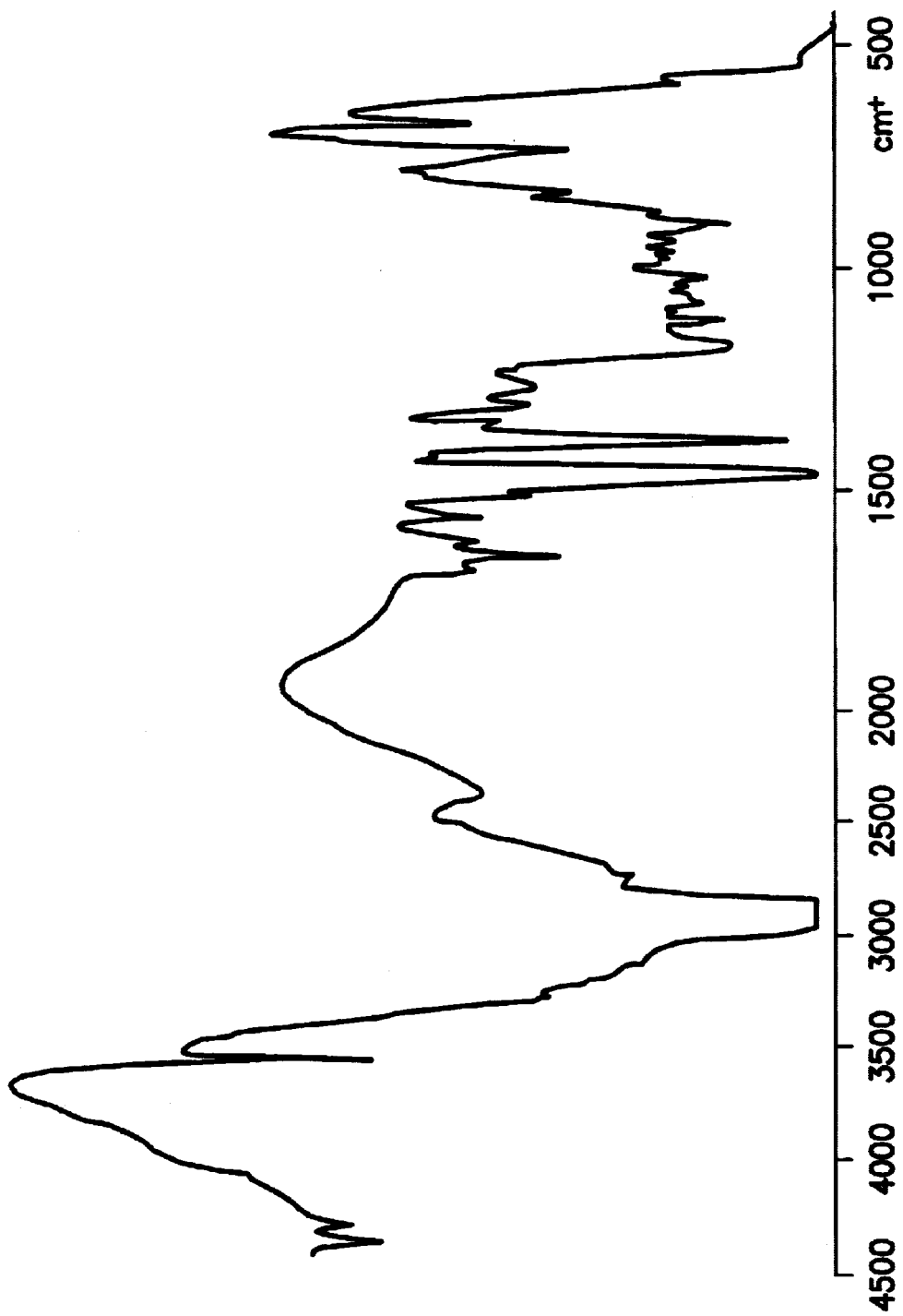
Figure 7A:
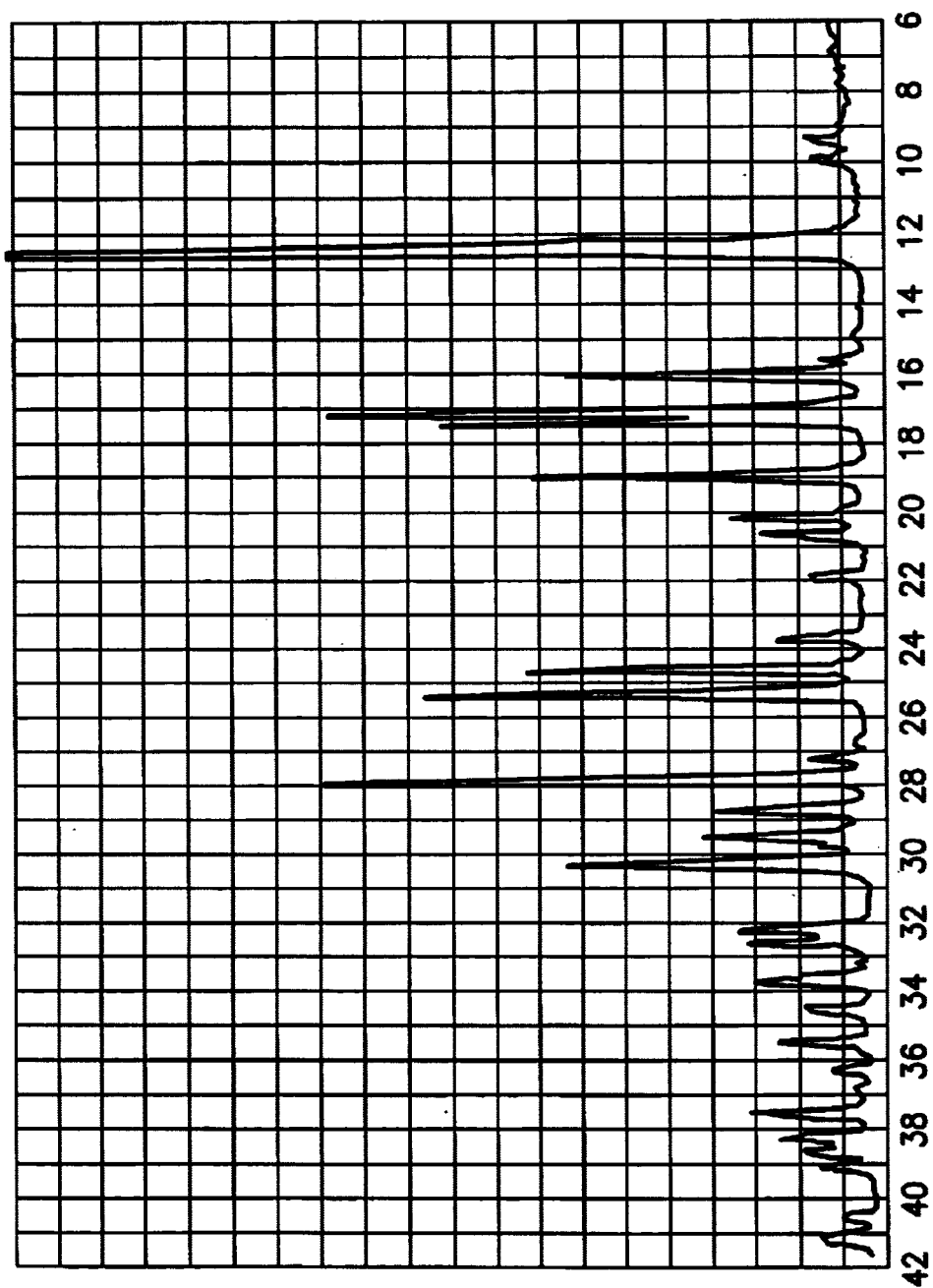
FIGS. 7a, 7b, and 7c show, respectively, the powder X-ray diffraction spectrum, the then-nograviometric (TGA) curve and the infrared spectrum of alendronate sodium Form G.
Figure 7B:
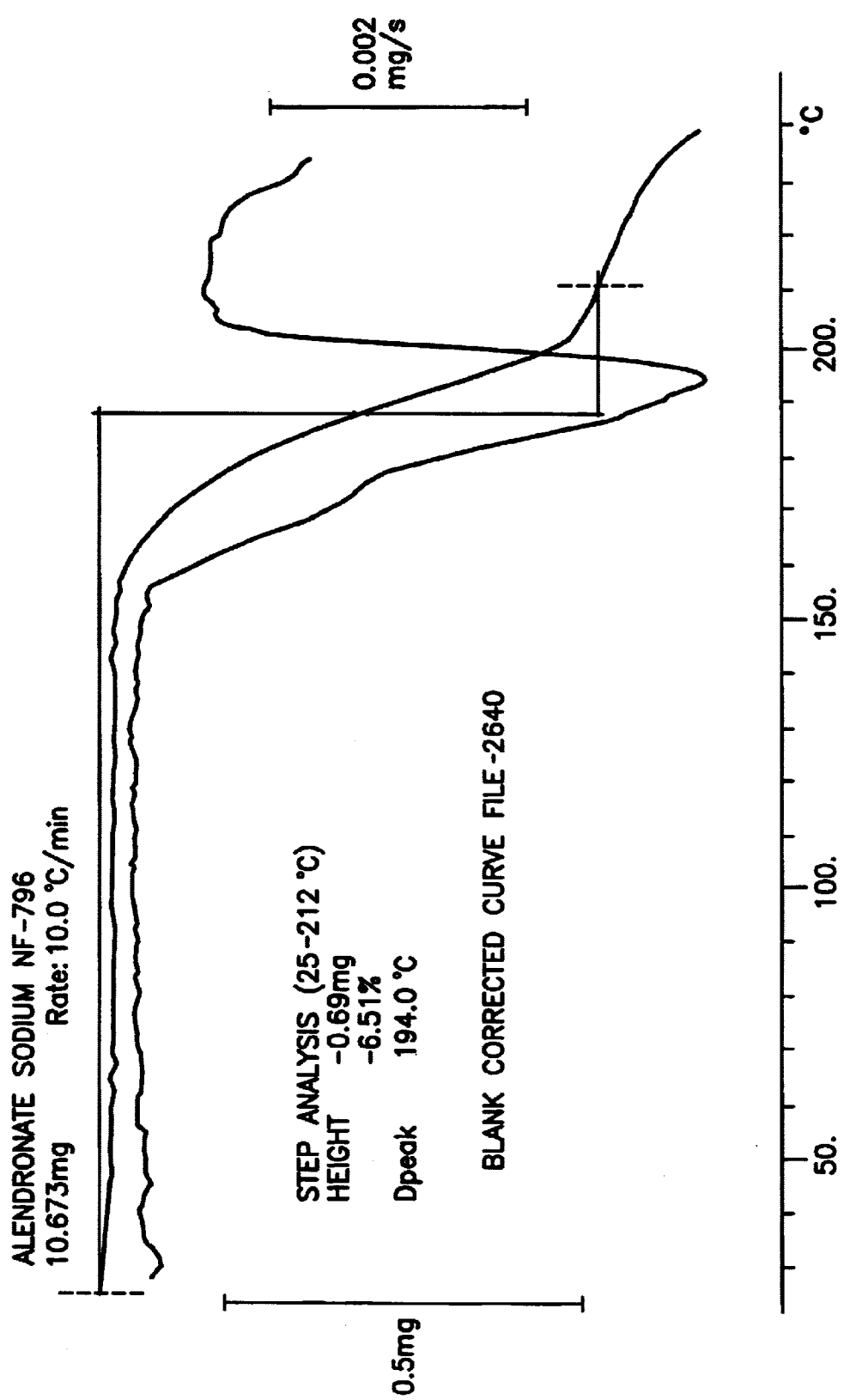
Figure 7C:
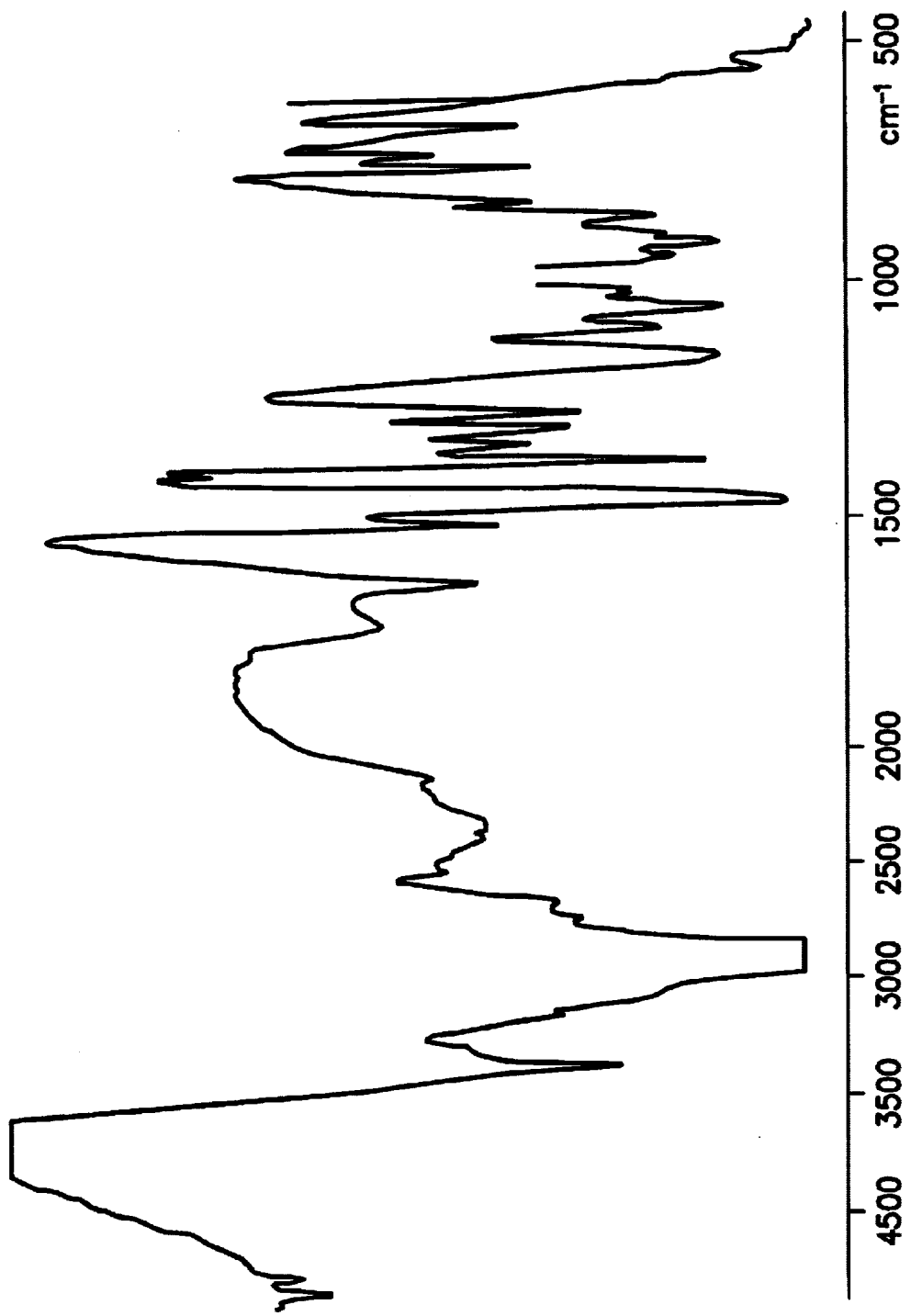
Figure 8A:
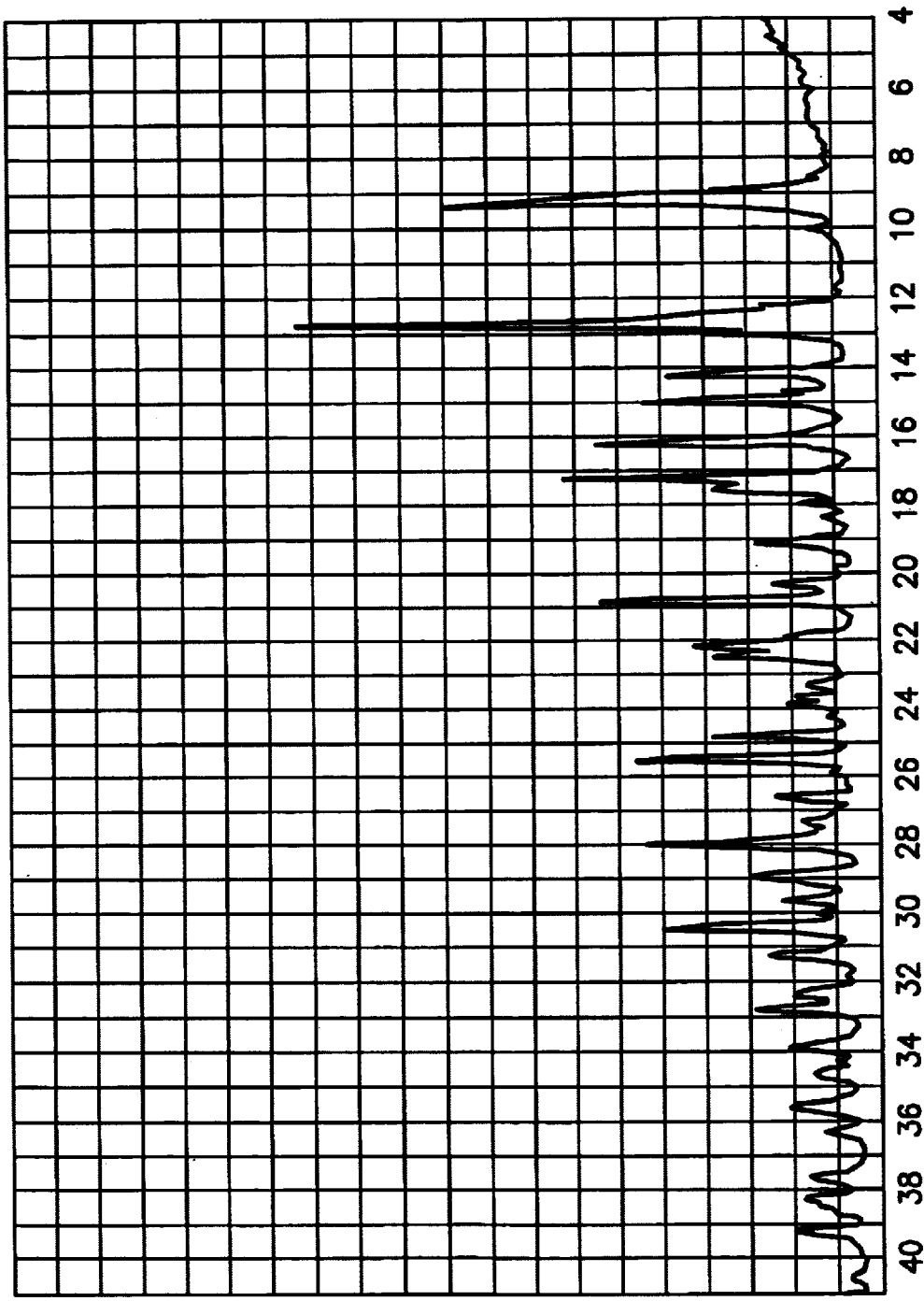
FIGS. 8a, 8b and 8c show respectively the powder X-ray diffraction spectrum, the thermograviometric (TGA) curve and the infrared spectrum of alendronate sodium of Form H.
Figure 8B:
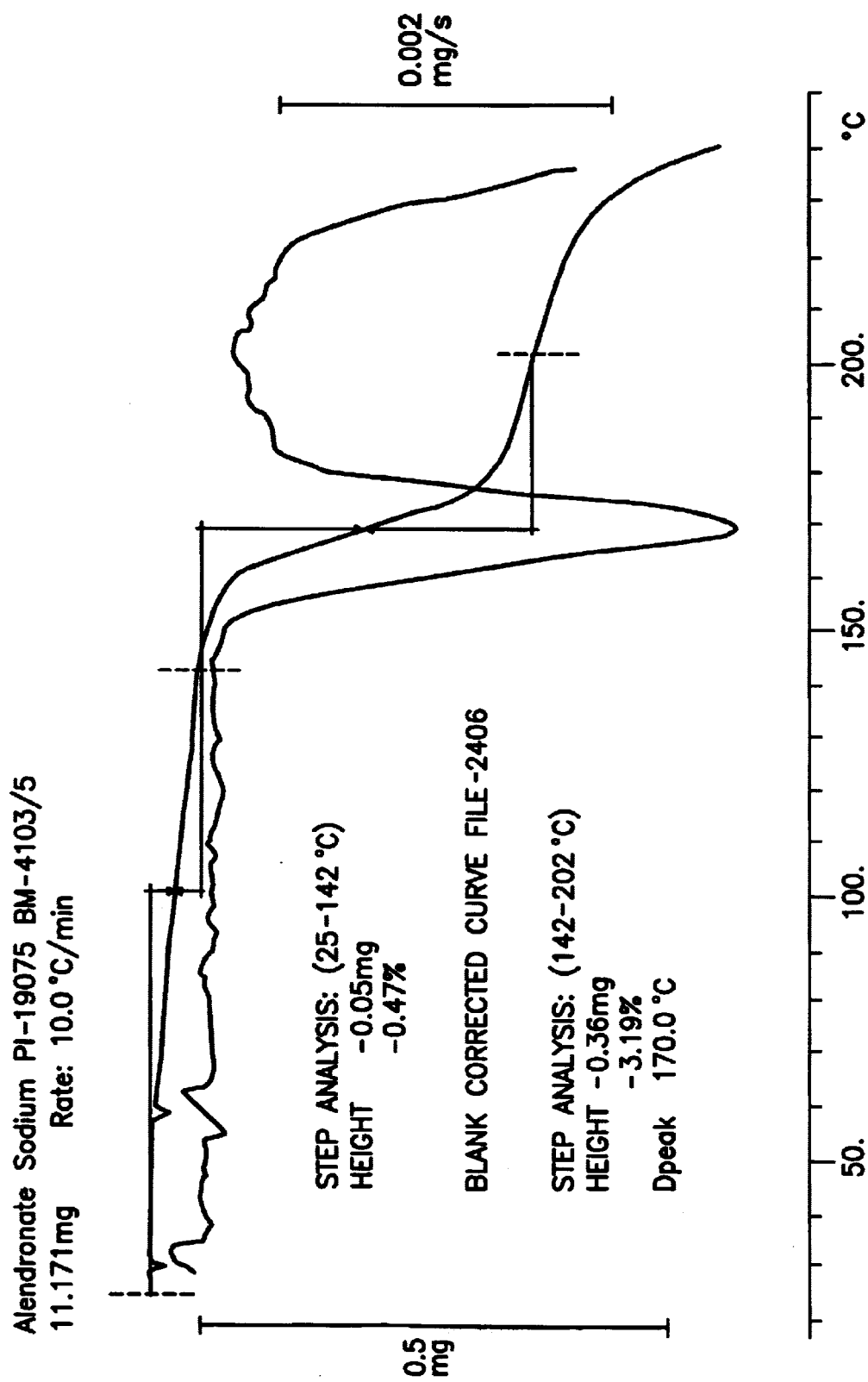
Figure 8C:
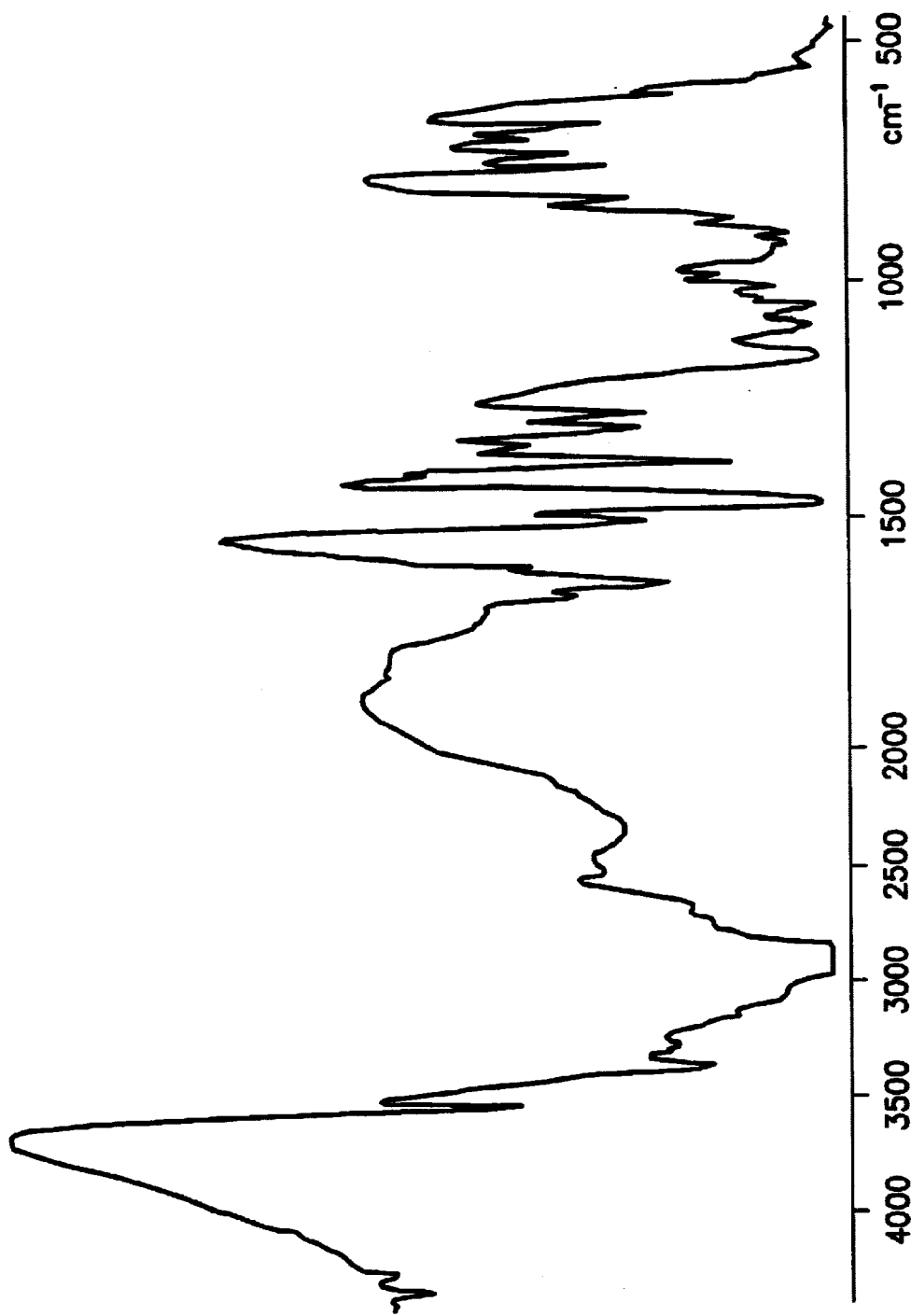

The invention discloses new hydrate forms of alendronate sodium having water contents of 1.3 percent to 11.7 percent.

The present invention also discloses new crystalline forms of alendronate sodium which have been designated Forms B, D, E, F, G and H.

The term "water content" refers to the content of water based upon the Loss on Drying method as described in Pharmacopeial Forum, Vol. 24, No. 1, page 5438 (January-Feburary 1998). The calculation of water content is based upon the percent of weight that is lost by drying. For Forms G and H the term "water content" refers to the content of water based upon a TGA measurement and a step analysis in the temperature range of about 25° C.–215° C. for Form G, and 25° C.–200° C. for Form H.

The term "lower alkanol" refers to alkanols having 1 to 4 carbon atoms. Preferred lower alkanols include ethanol, methanol and isopropanol.

The term "equivalents of water" means molar equivalents of water.

The term "equivalents of sodium base" means molar equivalents of sodium base.

Those skilled in the art will appreciate that the term "monohydrate" when used in reference to alendronic acid describes a crystalline material having a water content of 6.7%. Those skilled in the art will also understand that the term "anhydrous" when used in reference to alendronic acid describes alendronic acid that is substantially free of water.

One of skill in the art will appreciate that the term "monohydrate" when used in reference to the monosodium salt of alendronic acid describes a crystalline material having a water content of approximately 6.2%.

One skilled in the art will also appreciate that the term "dihydrate" when used in reference to the monosodium salt of alendronic acid describes a crystalline material having a water content of approximately 11.7%.

One skilled in the art will also appreciate that the term "1/4 hydrate" when used in reference to the monosodium salt of alendronic acid describes a crystalline material having a water content of approximately 1.6%.

One skilled in the art will also appreciate that the term "1/3 hydrate" when used in reference to the monosodium salt of alendronic acid describes a crystalline material having a water content of approximately 2.1%.

One skilled in the art will also appreciate that the term "hemihydrate" when used in reverence to the monosodium salt of alendronic acid describes a crystalline material having a water content of approximately 3.2%.

One skilled in the art will also appreciate that the term "2/3 hydrate" when used in reference to the monosodium salt of alendronic acid describes a crystalline material having a water content of approximately 4.2%.

One skilled in the art will also appreciate that the term "3/4 hydrate" when used in reference to the monosodium salt of alendronic acid describes a crystalline material having a water content of approximately 4.7%.

One skilled in the art will also appreciate that the term "5/4 hydrate" when used in reference to the monosodium salt of alendronic acid describes a crystalline material having a water content of approximately 7.6%.

One skilled in the art will also appreciate that the term "4/3 hydrate" when used in reference to the monosodium salt of alendronic acid describes a crystalline material having a water content of approximately 8.1%.

One skilled in the art will also appreciate that the term "3/2 hydrate" when used in reference to the monosodium salt of alendronic acid describes a crystalline material having a water content of approximately 9.1%.

Finally, those skilled in the art will appreciate that the term "trihydrate" when used in reference to the monosodium salt of alendronic acid refers to a crystalline material having a water content of approximately 16.6%.

The term "sodium base" refers to sodium hydroxide and the sodium alkoxide of a lower alkanol.

Alendronic acid can be prepared by methods that are well known in the art. MI Kabachnik et al., Izv. Akad. Nauk USSR, Ser. Khim, 2, 433 (1978) discloses a reaction for making alendronic acid;

Alendronic acid can also be prepared by the process disclosed in U.S. Pat. No. 4,621,077. It will be appreciated that when alendronic acid is recrystallized from water, as in the above process, the monohydrate is formed.

Alendronate sodium trihydrate can be prepared by the process disclosed in U.S. Pat. No. 4,922,007.

The contents of all references cited are incorporated by reference.

Alendronic acid monohydrate can be converted to alendronic acid anhydrous by heating in a vacuum oven at 110–220° C. at a vacuum of less than 5 mm Hg for 24 hours.

In accordance with the process aspect of the present invention, alendronic acid anhydrous as prepared by any of the known methods is added to a lower alkanol, preferably ethanol, together with a sodium base, preferably sodium hydroxide, and an amount of water that depends upon the desired crystal form of alendronate sodium. The molar ratio of sodium base to alendronic acid is 1:1. Those skilled in the art will appreciate that a higher ratio of NaOH would yield the undesirable disodium and trisodium salts. The reaction mixture is boiled under reflux while being stirred vigorously for approximately 15 hours, until the pH of the liquid phase remains constant (approx. pH 7). Crystalline alendronate sodium is then isolated, preferably by filtration after cooling to ambient temperature, washing with absolute ethanol, optionally washing with absolute ethyl ether and drying overnight in a vacuum oven at ambient temperature and at a pressure of 10 mm to 15 mm of mercury. For the purposes of this specification, ambient temperature is from about 20° C. to about 25° C.

In accordance with the aspects of this invention wherein alendronic acid monohydrate is converted to,alendronate sodium, alendronic acid monohydrate as prepared by any of the known methods is added to an alkanol, preferably ethanol, together with a sodium base, preferably sodium hydroxide, and a desired amount of water. The amount of water depends upon the crystal form that is desired. The molar ratio of sodium base to alendronic acid is 1:1. The reaction mixture is boiled under reflux while stirring vigorously for approximately 15 hours, until the pH of the liquid phase remains constant (approx. pH 7). Crystalline alendronate sodium is then isolated, preferably by filtration after cooling to ambient temperature followed by washing with absolute ethanol, washing with absolute ether and drying overnight in a vacuum oven at ambient temperature and at a pressure of 10 mm to 15 mm of mercury.

In accordance with the aspects of this invention wherein alendronate sodium trihydrate (Form C) is converted to alendronate sodium dihydrate (Form C), alendronate sodium trihydrate as prepared by methods known in the art is added to an alkanol which is substantially free of water, preferably absolute ethanol. This mixture is treated with a drying agent, preferably by refluxing the mixture in a reflux condenser wherein the condensate formed passes through 3 Å molecular sieves. The weight:weight ratio of molecular sieves to alendronate sodium trihydrate is preferably about 2:1 and most preferably 12:5. Refluxing of the mixture is preferably done for 24 hours with stirring. Alendronate sodium dihydrate is then isolated, preferably by filtration after cooling to ambient temperature, washing with absolute ether and drying overnight in a vacuum oven at ambient temperature and at a pressure of 10 mm to 15 mm of mercury.

In accordance with the aspects of this invention wherein alendronate sodium trihydrate (Form C) is converted to alendronate sodium monohydrate (Form C), alendronate sodium trihydrate as prepared by any of the methods known in the art is added to an alkanol which is substantially free of water, preferably absolute ethanol. This mixture is treated with a drying agent, preferably by refluxing the mixture in a reflux condenser wherein the condensate formed passed through 3 Å molecular sieves. If and when a first portion of molecular sieves is exhausted, a second portion of fresh molecular sieves is used. The weight:weight ratio of molecular sieves to alendronate sodium trihydrate is preferably about 2:1 and most preferably 12:5. Refluxing of the mixture is preferably done for 24 hours with stirring. The mixture is allowed to cool to ambient temperature before recharging with an equivalent amount of molecular sieves. Alendronate sodium monohydrate is then isolated, preferably by cooling to ambient temperature, filtration, washing with absolute ether and drying overnight in a vacuum oven at ambient temperature and a pressure of 10 mm and 15 mm of mercury.

In accordance with the present invention, the new crystalline forms of alendronate sodium and the new hydrate forms of alendronate sodium may be prepared as pharmaceutical compositions which are particularly useful for the treatment of bone resorption in bone diseases including osteoporosis and Paget's disease. Such compositions may comprise one of the new crystalline and hydrate forms of alendronate sodium with pharmaceutically acceptable carriers and/or excipients.

For example, these compositions may be prepared as medicaments to be administered orally, parenterally, rectally, transdermally, bucally, or nasally. Suitable forms for oral administration include tablets, compressed or coated pills, dragees, sachets, hard or gelatin capsules, sub-lingual tablets, syrups and suspensions; for parenteral administration the invention provides ampoules or vials that include an aqueous or nonaqueous solution or emulsion; for rectal administration there are provided suppositories with hydrophilic or hydrophobic vehicles; and for topical application as ointments or aerosol formulations known in the art; transdermal delivery there are provided suitable delivery systems as known in the art; and for nasal delivery there are provided suitable aerosol delivery systems known in the art.

The powder X-ray diffraction patterns were obtained by methods known in the art using a Philips X-Ray powder diffractometer, Goniometer model 1050/70 at a scanning speed of 2° per minute.

The thermogravimetric curves were obtained by methods known in the art using a Mettler TGA TG50. The weight of the samples was about 10 mg. The temperature range was from 25° C. to at least 200° C., at the rate of 10° C./min. Samples were purged with nitrogen gas at a flow rate of 40 ml/min. Standard 150 ml aluminum crucibles were used.

The infrared spectra were obtained by methods known in the art using a Perkin Elmer FT-IR Paragon 1000 spectrometer. Samples were analyzed in Nujol mulls. Spectra were obtained at 4 cm$^{-1}$ resolution and 16 scans each.

The atomic absorption analysis was obtained by methods known in the art using a Perkin Elmer 5000 Flame Atomic Absorption instrument. Sodium content was determined against standard solutions obtained from Merck and Aldrich.

EXAMPLES

This invention will be better understood from the experimental details which follow. However, one skilled in the art will readily appreciate that the specific methods and results discussed are merely illustrative of the invention as described more fully in the claims that follow thereafter.

Example 1

Preparation of Alendronic Acid Monohydrate

Alendronic acid was crystallized from water to make alendronic acid monohydrate. The resulting alendronic acid monohydrate was dried at 50° C. at 10 mm Hg pressure for 15 hours to give dry alendronic acid monohydrate containing 6.9% water.

Example 2

Preparation of Anhydrous Alendronic Acid

The alendronic acid monohydrate from Example 1 was further dried at 110–120° C. in 1 mm Hg for 4 hours to give anhydrous alendronic acid. The water content was 0.3% by weight.

Example 3

Preparation of Alendronate Sodium from Anhydrous Alendronic Acid

A 250 ml flask was fitted with a mechanical stirrer, a thermometer, and a reflux condenser. The flask was charged with 41.1 ml of a solution of sodium hydroxide in ethanol (0.49N, 20.1 mmol), 8.9 ml of ethanol, water (0 to 40 mol. eq., according to the crystal form desired), and 5 g (20.1 mmol) of anhydrous alendronic acid. The reaction mixture was boiled with vigorous stirring for about 15 hours until the of pH of the liquid phase remained constant (approx. pH 7). After cooling of the reaction mixture to ambient temperature, the solid material was filtered, washed with absolute ethanol, and dried overnight in a vacuum oven (10–15 mmHg, ambient temperature) to give 96–99% sodium alendronate having the following crystal forms: crystal Form D, when 0–4 (preferably 0–2) mol. eq. water were used; crystal Form F, when 5–8 (preferably 6–7) mol. eq. water were used; crystal Form E, when 9–15 (preferably 12) mol. eq. water were used; and crystal Form G, when 15–40 (preferably 25–35) mol. eq. water were used. The monosodium salt was confirmed by atomic absorption and by measuring the pH of a 0.5% aqueous solution of the salt (approx. pH 4.4).

Example 4

Preparation of Alendronate Sodium from Alendronic Acid Monohydrate

A 250 ml flask was fitted with a mechanical stirrer, a thermometer, and a reflux condenser. The flask was charged with 38.2 ml of a solution of sodium hydroxide in ethanol (0.49 N, 18.7 mmol), 4.8 ml of ethanol, water (0 to 100 mol. eq., according to the crystal form desired), and 5 g (18.7 mmol) of alendronic acid monohydrate. The reaction mixture was boiled with vigorous stirring for about 15 hours until stability of pH of the liquid phase was reached (approx. pH 7). After cooling of the reaction mixture to ambient temperature the precipitate was filtered, washed with absolute ethanol, and dried overnight in a vacuum over (10–15 mm Hg, ambient temperature) to give 96–99% sodium alendronate having the following crystalline forms: crystalline Form B, when 0–4 (preferably 0–2) mol. eq. water were used; crystalline Form F, when 3–5 mol. eq. water were used; crystalline Form E, when 11–13 (preferably 12) mol. eq. water were used; and crystalline Form G, when 15–100 (preferably 20–80) mol. eq. water were used.

The monosodium salt was confirmed by atomic absorption and by measuring the pH of a 0.5% aqueous solution of the salt (approx. pH 4.4).

The water content is determined using the TGA technique, heating the sample to 230° C. and calculating the sharp LOD (loss on drying) step, which occurs above 150° C.

Example 5

Preparation of Sodium Alendronate Dihydrate

A one liter flask was fitted with a magnetic bar stirrer, Soxhlet extraction funnel (operating volume 150 ml) charged with 3 Å molecular sieves (60 g), and reflux condenser connected to a drying tube with 3 Å molecular sieves. The flask was charged with sodium alendronate trihydrate (25 g) and absolute ethanol (450 ml, vol. % of water<0.1%). The mixture was boiled with stirring for 24 hours. After cooling to ambient temperature the solid material was filtered, washed with absolute ethyl ether, and dried overnight in a vacuum oven (10–15 mm Hg, ambient temperature) to give sodium alendronate dihydrate.

Example 6

Preparation of Sodium Alendronate Monohydrate

A one liter flask was fitted with a magnetic bar stirrer, Soxhlet extraction funnel (operating volume 150 ml) charged with 3 Å molecular sieves (60 g), and reflux condenser connected to a drying tube with 3 Å molecular sieves. The flask was charged with sodium alendronate trihydrate (25 g) and absolute ethanol (450 ml, vol. % of water<0.1%). The mixture was boiled with stirring for, 24 hours. After cooling to ambient temperature, the used molecular sieves were replaced by a new portion of 3 Å molecular sieves (60 g) and the reflux was continued for additional 24 hours. After cooling to ambient temperature the solid material was filtered, washed with absolute ethyl ether, and dried overnight in a vacuum oven (10–15 mm Hg, ambient temperature) to give sodium alendronate monohydrate.

Example 7

Preparation of Alendronate Sodium Form G from Alendronic Acid Monohydrate

Preparation of aqueous ethanolic sodium hydroxide:
Absolute ethanol (250 ml) and water (59 ml, 35×0.094 mol) were mixed. Sodium hydroxide (3.8 g, assay 99%, 0.094 mol) was dissolved in 45 ml of this aqueous ethanol. The remaining aqueous ethanol was used to prepare a suspension of alendronic acid monohydrate.

A one liter flask was fitted with a mechanical stirrer, a thermometer, and a reflux condenser. The flask was charged with alendronic acid monohydrate (25 g, 0.094 mol) and aqueous ethanol. The mixture was heated to boiling with stirring. The aqueous ethanolic sodium hydroxide was added dropwise to the suspension of alendronic acid monohydrate in aqueous ethanol for 3 hours at reflux with vigorously stirring. Then the mixture was stirred at reflux for additional 15 hours. The mixture was cooled to room temperature with stirring. The solid was filtered, washed with absolute ethanol, then with absolute ethyl ether, and dried overnight in a vacuum oven (10–15 mm Hg, ambient temperature) to give 26.2 g of alendronate sodium, having crystalline Form G.

Example 8

Preparation of Alendronate Sodium Form G from Alendronic Acid Monohydrate

Preparation of aqueous ethanolic sodium hydroxide:

Absolute ethanol (250 ml) and water (59 ml, 35×0.094 mol) were mixed. Sodium hydroxide (3.8 g, assay 99%, 0.094 mol) was dissolved in 45 ml of this aqueous ethanol. The remaining aqueous ethanol was used to prepare a suspension of alendronic acid monohydrate.

A one liter flask was fitted with a mechanical stirrer, a thermometer, and a reflux condenser. The flask was charged with alendronic acid monohydrate (25 g, 0.094 mol) and aqueous ethanol. The mixture was heated to boiling with stirring. The aqueous ethanolic sodium hydroxide was added dropwise to the suspension of alendronic acid monohydrate in aqueous ethanol for 3 hours at reflux with vigorously stirring. Then the mixture was stirred at reflux for additional 15 hours. The mixture was cooled to room temperature with stirring. The solid was filtered, washed with absolute ethanol, and dried overnight in a vacuum oven (10–15 mm Hg, ambient temperature) to give 26.2 g of alendronate sodium, having crystalline Form G.

Example 9

Preparation of Alendronate Sodium Form G from Alendronic Acid Monohydrate

Preparation of aqueous ethanolic sodium hydroxide:

Absolute ethanol (250 ml) and water (59 ml, 35×0.094 mol) were mixed. Sodium hydroxide (3.8 g, assay 99%, 0.094 mol) was dissolved in 45 ml of this aqueous ethanol. The remaining aqueous ethanol was used to prepare a suspension of alendronic acid monohydrate.

A one liter flask was fitted with a mechanical stirrer, a thermometer, and a reflux. condenser. The flask was charged with alendronic acid monohydrate (25 g, 0.094 mol) and aqueous ethanol. The mixture was heated to boiling with stirring. The aqueous ethanolic sodium hydroxide was added dropwise to the suspension of alendronic acid monohydrate in aqueous ethanol for 3 hours at reflux with vigorously stirring. Then the mixture was stirred at reflux for additional 15 hours. The mixture was cooled to room temperature with stirring. The solid was filtered, washed with absolute ethanol, and dried overnight in a vacuum oven (10–15 mm Hg, 40–50° C.) to give 26.2 g of alendronate sodium, having crystalline Form G.

Example 10

Preparation of Alendronate Sodium Form G from Alendronic Acid Monohydrate

Preparation of aqueous ethanolic sodium hydroxide:

Absolute ethanol (250 ml) and water (59 ml, 35×0.094 mol) were mixed. Sodium hydroxide (3.8 g, assay 99%, 0.094 mol) was dissolved in 45 ml of this aqueous ethanol. The remaining aqueous ethanol was used to prepare a suspension of alendronic acid monohydrate.

A one liter flask was fitted with a mechanical stirrer, a thermometer, and a reflux condenser. The flask was charged with alendronic acid monohydrate (25 g, 0.094 mol) and aqueous ethanol. The mixture was heated to boiling with stirring. The aqueous ethanolic sodium hydroxide was added dropwise to the suspension of alendronic acid monohydrate in aqueous ethanol for 3 hours at reflux with vigorously stirring. Then the mixture was stirred at reflux for additional 15 hours. The mixture was cooled to room temperature with stirring. The solid was filtered, washed with absolute ethanol, then with absolute ethyl ether, and dried overnight in a vacuum oven (10–15 mm Hg, 40–50° C.) to give 26.2 g of alendronate sodium, having crystalline Form G.

Example 11

Preparation of Alendronate Sodium Form (G) from Alendronate Sodium Trihydrate

A suspension of alendronate sodium trihydrate 1.0 g (3.08 mmol) in aqueous ethanol (10 ml of ethanol+1.9 ml of water) was boiled at reflux with stirring for 15 hrs. After cooling to ambient temperature the solid was filtered, washed with absolute ethanol and ether, and dried overnight in a vacuum oven (10–15 mm Hg, ambient temperature) to give 0.9 g of alendronate sodium, containing crystal form G.

Example 12

Preparation of Alendronate Sodium Form H from Alendronic Acid Monohydrate

Preparation of aqueous ethanolic sodium hydroxide:

Absolute ethanol (50 ml) and water (6.7 ml, 20×0.019 mol) were mixed. Sodium hydroxide (0.76 g, assay 99%, 0.019 mol) was dissolved in 8.5 ml of this aqueous ethanol. The remaining aqueous ethanol was used to prepare a suspension of alendronic acid monohydrate.

A 250 ml flask was fitted with a mechanical stirrer, a thermometer, a dropping funnel, and a reflux condenser. The flask was charged with alendronic acid monohydrate (5 g, 0.019 mol) and aqueous ethanol. The aqueous ethanolic sodium hydroxide was added dropwise to the suspension of alendronic acid monohydrate in aqueous ethanol for 15 minutes at reflux with vigorously stirring. The mixture was then refluxed for additional 15 hours. The mixture was then cooled to room temperature with stirring. The solid was filtered, washed with absolute ethanol, then with absolute ethyl ether, and dried overnight in a vacuum oven (10–15 mm Hg, ambient temperature) to give 5.2 g of alendronate sodium, having crystalline Form H.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

We claim:

1. Crystalline monosodium alendronate 2/3 hydrate.
2. The crystalline monosodium alendronate 2/3 hydrate of claim 1 having a water content of about 4.2 weight percent.
3. A crystalline monosodium alendronate 2/3 hydrate having an X-ray powder diffraction pattern with characteristic peaks at 13.1±0.2, 15.2±0.2, 16.3±0.2, 22.3±0.2, 22.5±0.2, 23.4±0.2 and 23.7±0.2 degrees 2 theta.

4. A crystalline monosodium alendronate 2/3 hydrate having infrared absorption bands at 662, 919, 934, 954, 1054, 1072, 1297 and 1318 cm$^{-1}$.

5. Crystalline monosodium alendronate hemihydrate.

6. Crystalline monosodium alendronate hemihydrate having an X-ray powder diffraction pattern with characteristic peaks at 7.0±0.2, 9.3±0.2 and 14.0±0.2 degrees 2 theta.

7. The crystalline monosodium alendronate hemihydrate of claim 6 having additional X-ray diffraction peaks at 11.8±0.2, 13.3±0.2, 15.3±0.2, 16.2±0.2, 17.4±0.2 and 19.4±0.2 degrees 2 theta.

8. A Crystalline monosodium alendronate hemihydrate having infrared absorption bands at 660, 897, 924, 953, 970, 1017, 1040, 1093, 1149, 1177, 1252, 1293, 1337, 1535, 1606 and 1639 cm$^{-1}$.

9. A Crystalline monosodium alendronate hemihydrate form H characterized by x-ray peaks at 9.2±0.2, 14.2±0.2, 15.0±0.2, 17.1±0.2, 20.7±0.2, 22.0±0.2, and 22.4±0.2 degrees two theta.

10. A Crystalline monosodium alendronate hemihydrate form H having infrared absorption bands at 664, 688, 722, 751, 863, 893, 918, 936, 984, 1010, 1036, 1052, 1092, 1157, 1273, 1303, 1338, 1499, 1598, 1636 and 1664 cm$^{-1}$.

11. Crystalline monosodium alendronate Form B.

12. The crystalline monosodium alendronate form B of claim 11 having an X-ray powder diffraction pattern with characteristic peaks at 12.2±0.2, 13.3±0.2, 14.8±0.2, 15.8±0.2, 16.3±0.2, 16.6±0.2 and 17.2±0.2 degrees 2 theta.

13. The crystalline monosodium alendronate form B of claim 12 having additional X-ray diffraction peaks at 19.4±0.2, 21.3±0.2, 22.6±0.2, 23.2±0.2, 24.0±0.2, 25.2±0.2, 25.8±0.2, 27.4±0.2, 29.4±0.2, and 36.0±0.2 degrees 2 theta.

14. The crystalline monosodium alendronate form B of claim 11 having infrared absorption bands at 654, 955, 1074, 1261, 1309, and 1614 cm$^{-1}$.

15. A process for preparing a hydrate of monosodium alendronate having about 1.3% to about 7.2% water comprising the steps of:
   forming the monosodium alendronate hydrate by reaction of alendronic acid with a sodium base in suspension in a liquid medium comprising a lower alkanol or a mixture of a lower alkanol and water, wherein the liquid medium comprises 3 equivalents or more of water, based on the number of equivalents of alendronic acid, and selected according to, and
   separating the liquid medium from the crystalline hydrate of monosodium alendronate.

16. The process of claim 15 wherein the sodium base is sodium hydroxide.

17. The process of claim 15 wherein the crystalline hydrate of monosodium alendronate is formed by providing a solution of the sodium base in a mixture comprising a lower alkanol and water, providing a suspension of the alendronic acid in a mixture of a lower alkanol and water and contacting the solution and the suspension.

18. The process of claim 15 wherein the monosodium alendronate hydrate is formed by providing a solution of the sodium base in a liquid medium comprising a lower alkanol, providing a suspension of the alendronic acid in a liquid medium comprising a mixture of a lower alkanol and water and contacting the solution and the suspension.

19. The process of claim 15 wherein the monosodium alendronate hydrate is formed by providing a solution of the sodium base in a liquid medium comprising mixture of a lower alkanol and water, providing a suspension of the alendronic acid in a lower alkanol and contacting the solution and the suspension.

20. A process of claim 15 wherein for making the crystalline monosodium alendronate 2/3 hydrate of claim 1 comprising the steps of:
   a) forming the crystalline monosodium alendronate 2/3 hydrate by reaction of alendronic acid with a sodium base in a liquid medium of a lower alkanol or a mixture of a lower alkanol and water, and
   b) separating the liquid medium from the crystalline monosodium alendronate 2/3 hydrate.

21. The process of claim 20 wherein the monosodium alendronate 2/3 hydrate has an X-ray diffraction pattern with characteristic peaks at 13.1±0.2, 15.2±0.2, 16.3±0.2, 22.3±0.2, 22.5±0.2, 23.4±0.2 and 23.7±0.2 degrees 2 theta and the liquid medium is a lower alkanol or a mixture of a lower alkanol and water in an amount of about 4 equivalents or less with respect to the alendronic acid.

22. The process of claim 21 wherein the amount of water is about 2 equivalents or less with respect to the alendronic acid.

23. The process of claim 21 wherein the alendronic acid is anhydrous and the amount of water is about 2 equivalents or less with respect to the alendronic acid.

24. The process of claim 15 the crystalline hydrate of monosodium alendronate has an X-ray diffraction pattern with characteristic peaks at 9.3±0.2, 11.7±0.2, 15.3±0.2, 16.2±0.2, 17.4±0.2 and 25.5±0.2 degrees 2 theta and the liquid medium is a mixture of a lower alkanol and water comprising about 3 to about 8 equivalents of water with respect to the alendronic acid used.

25. The process of claim 24 wherein the alendronic acid is anhydrous and the amount of water is from about 6 to about 7 equivalents with respect to the alendronic acid.

26. A process for making monosodium alendronate hemihydrate of claim 5 comprising the steps of:
   a) forming the monosodium alendronate hemihydrate by reaction of alendronic acid with a sodium base in a liquid medium of a lower alkanol or a mixture of a lower alkanol and water, and
   b) separating the liquid medium from the monosodium alendronate hemihydrate, wherein
      the liquid medium is a mixture of a lower alkanol and from about 9 to about 35 equivalents of water with respect to the alendronic acid.

27. The process of claim 26 wherein the monosodium alendronate hemihydrate has an X-ray diffraction pattern with characteristic peaks at 7.0±0.2, 9.3±0.2 and 14.0±0.2 degrees 2 theta and the liquid medium is a mixture of a lower alkanol and water in an amount of from about 9 to about 15 equivalents with respect to the alendronic acid.

28. The process of claim 27 wherein the alendronic acid is alendronic acid monohydrate and the amount of water is from about 11 to about 13 equivalents with respect to the alendronic acid.

29. The process of claim 27 where the amount of water is about 12 equivalents with respect to the alendronic acid.

30. The process of claim 26 wherein the liquid medium is a mixture of a lower alkanol and water in an amount of from about 20 to about 35 equivalents with respect to the alendronic acid.

31. The process of claim 30 wherein the amount of water is about 20 equivalents with respect to the alendronic acid.

32. The process of claim 30 wherein the monosodium alendronate hemihydrate produces an X-ray powder diffraction pattern with characteristic peaks at 9.2±0.2, 14.2±0.2, 15.0±0.2, 17.1±0.2, 20.7±0.2, 22.0±0.2, and 22.4±0.2 degrees two theta.

33. The process of claim 32 wherein the monosodium alendronate hemihydrate has infrared absorption bands at 664, 688, 722, 751, 863, 893, 918, 936, 984, 1010, 1036, 1052, 1092, 1157, 1273, 1303, 1338, 1499, 1598, 1636, and 1664 cm$^{-1}$.

34. A process for preparing the monosodium alendronate hydrate form B of claim 11 the steps of:
  forming the monosodium alendronate monohydrate by reaction of alendronic acid with a sodium base in a liquid medium of a lower alkanol or a mixture of a lower alkanol and water, and
  separating the liquid medium from the monosodium alendronate monohydrate.

35. The process of claim 34 wherein the alendronic acid is alendronic acid monohydrate and the liquid medium is a lower alkanol or a mixture of a lower alkanol and water in an amount of about 4 equivalents or less with respect to the alendronic acid.

36. The process of claim 34 wherein liquid medium is a lower alkanol.

37. The process of claim 36 wherein the monosodium alendronate monohydrate is formed by providing a solution of the sodium base in a lower alkanol, providing a suspension of the alendronic acid in a lower alkanol and contacting the solution and the suspension.

* * * * *